United States Patent
May et al.

(10) Patent No.: US 11,247,837 B1
(45) Date of Patent: Feb. 15, 2022

(54) DISPENSER ACTUATOR ASSEMBLY

(71) Applicant: James Alexander Corporation, Blairstown, NJ (US)

(72) Inventors: Richard James May, Saylorsburg, PA (US); Jeffrey Rendano, Kunkletown, PA (US)

(73) Assignee: James Alexander Corporation, Blairstown, NJ (US)

( * ) Notice: Subject to any disclaimer, the term of this patent is extended or adjusted under 35 U.S.C. 154(b) by 177 days.

(21) Appl. No.: 16/654,192

(22) Filed: Oct. 16, 2019

Related U.S. Application Data

(63) Continuation-in-part of application No. 15/683,523, filed on Aug. 22, 2017, now Pat. No. 10,518,930, and
(Continued)

(51) Int. Cl.
*B65D 83/00* (2006.01)
*B65D 81/32* (2006.01)
(Continued)

(52) U.S. Cl.
CPC ......... *B65D 83/0055* (2013.01); *B65D 35/36* (2013.01); *B65D 47/2037* (2013.01);
(Continued)

(58) Field of Classification Search
CPC ... A61M 35/003; A61M 35/006; B65D 25/08; B65D 35/28; B65D 47/2037; B65D 35/242; B65D 35/36; B65D 47/3244; B65D 81/3266; B65D 83/00; B65D 83/0005; B65D 47/2031; B65D 81/3244; B05C 17/00553; B05C 17/00583; B05C 17/00586
(Continued)

(56) References Cited

U.S. PATENT DOCUMENTS

| | | |
|---|---|---|
| 3,450,319 A | 6/1969 | Ray et al. |
| 5,538,353 A | 7/1996 | DeHavilland |

(Continued)

*Primary Examiner* — David J Walczak
(74) *Attorney, Agent, or Firm* — Paul J. Nykaza; Schacht Law Office, Inc.

(57) ABSTRACT

A dispenser actuator assembly (100) actuates a dispenser (10). The dispenser (10) is a plastic ampoule (10) having a container (48) having an outer wall (50) and membrane (52) collectively defining a first chamber (54) containing a flowable material (M). The membrane (52) has a weld seam (56). The actuator assembly (100) has a base member (102) configured to mount on the container (48). A fracturing mechanism (116) is operably connected to the base member (102). The fracturing mechanism (116) has a first extending member (132*a*) and a second extending member (132*b*), the first extending member (132*a*) and the second extending member (132*b*) positioned on the base member (102) in opposed relation. Each extending member (132*a*,132*b*) has a projection (150*a*,150*b*) positioned proximate the membrane (52). In response to deflection of the extending members (132*a*,132*b*) towards one another, the projections (150*a*,150*b*) are configured to deflect the outer wall (50) proximate the membrane (52) wherein the weld seam (56) fractures to create an opening through the membrane (56) to allow the flowable material (M) to pass therethrough.

34 Claims, 16 Drawing Sheets

Related U.S. Application Data a continuation-in-part of application No. 15/681,992, filed on Aug. 21, 2017, now Pat. No. 10,689,152, and a continuation-in-part of application No. 15/681,973, filed on Aug. 21, 2017, now Pat. No. 10,669,065.

(60) Provisional application No. 62/746,374, filed on Oct. 16, 2018.

(51) Int. Cl.
*B65D 47/20* (2006.01)
*B65D 35/36* (2006.01)
*B05C 17/005* (2006.01)

(52) U.S. Cl.
CPC .... *B65D 81/3266* (2013.01); *B05C 17/00583* (2013.01); *B05C 17/00586* (2013.01)

(58) Field of Classification Search
USPC .................................. 401/132–135, 158, 165
See application file for complete search history.

(56) References Cited

U.S. PATENT DOCUMENTS

| | | | |
|---|---|---|---|
| D386,849 S | 11/1997 | DeHavilland | |
| 5,772,346 A | 6/1998 | Edwards | |
| 6,283,933 B1 | 9/2001 | D'Alessio et al. | |
| 6,315,165 B1 | 11/2001 | Regan | |
| 6,536,975 B1 | 3/2003 | Tufts | |
| 6,539,975 B2 * | 4/2003 | Hedenberg | A61M 16/0075 138/26 |
| 6,641,319 B2 | 11/2003 | May | |
| 6,729,786 B1 * | 5/2004 | Tufts | A45D 34/04 401/132 |
| 6,991,393 B2 | 1/2006 | Tufts et al. | |
| 6,991,394 B2 | 1/2006 | Tufts et al. | |
| 7,182,536 B2 | 2/2007 | Tufts et al. | |
| 7,241,065 B2 | 7/2007 | Tufts et al. | |
| 7,306,390 B2 | 12/2007 | Quintero et al. | |
| 7,422,388 B2 | 9/2008 | Tufts et al. | |
| 7,516,872 B2 | 4/2009 | Boone et al. | |
| 7,581,899 B2 | 9/2009 | May et al. | |
| 7,824,122 B2 | 11/2010 | Flores et al. | |
| 7,909,808 B2 | 3/2011 | Stenton | |
| 7,976,234 B2 | 7/2011 | May | |
| 7,993,066 B2 | 8/2011 | Flores et al. | |
| D651,339 S | 12/2011 | Kirk, III et al. | |
| 8,323,260 B2 | 12/2012 | Stenton | |
| 8,342,765 B2 | 1/2013 | Stenton | |
| 8,403,178 B2 | 3/2013 | May et al. | |
| 8,491,212 B2 | 7/2013 | Castel et al. | |
| 8,518,076 B2 | 8/2013 | Stenton | |
| 8,702,751 B2 | 4/2014 | Stenton | |
| 8,794,858 B2 * | 8/2014 | Kirk, III | B05B 11/048 401/135 |
| 8,801,312 B2 | 8/2014 | Guzman et al. | |
| 8,807,859 B2 | 8/2014 | Stenton | |
| 8,864,399 B2 | 10/2014 | Guzman et al. | |
| 9,089,870 B2 | 7/2015 | Frazier | |
| 9,119,946 B2 | 9/2015 | Dokken et al. | |
| 9,265,923 B2 | 2/2016 | Boone et al. | |
| 9,486,829 B2 | 11/2016 | Kirk, III et al. | |
| 9,675,787 B2 | 6/2017 | Guzman | |
| 10,392,163 B2 | 8/2019 | May et al. | |
| 10,518,930 B2 | 12/2019 | May et al. | |
| 10,526,110 B2 | 1/2020 | May et al. | |
| 10,543,956 B2 | 1/2020 | May et al. | |
| 10,603,019 B2 | 3/2020 | Miller et al. | |
| 10,669,065 B2 | 6/2020 | May et al. | |
| 10,689,152 B2 | 6/2020 | May et al. | |
| 2003/0068189 A1 | 4/2003 | Tsaur | |
| 2004/0254561 A1 | 12/2004 | Stenton | |
| 2005/0111900 A1 | 5/2005 | Fazzolari et al. | |
| 2008/0046004 A1 | 2/2008 | Stenton | |
| 2008/0167681 A1 * | 7/2008 | Stenton | A61B 17/00491 606/214 |
| 2008/0195040 A1 | 8/2008 | Clark et al. | |
| 2009/0311030 A1 | 12/2009 | Stenton | |
| 2013/0004230 A1 | 1/2013 | Kirk, III et al. | |
| 2014/0133895 A1 | 5/2014 | Dockery | |
| 2015/0306362 A1 | 10/2015 | Battaglia | |
| 2017/0049210 A1 | 2/2017 | Kirk, III et al. | |
| 2017/0354406 A1 | 12/2017 | Miller et al. | |
| 2018/0050858 A1 | 2/2018 | May et al. | |
| 2018/0065776 A1 | 3/2018 | May et al. | |
| 2018/0065783 A1 | 3/2018 | May et al. | |

* cited by examiner

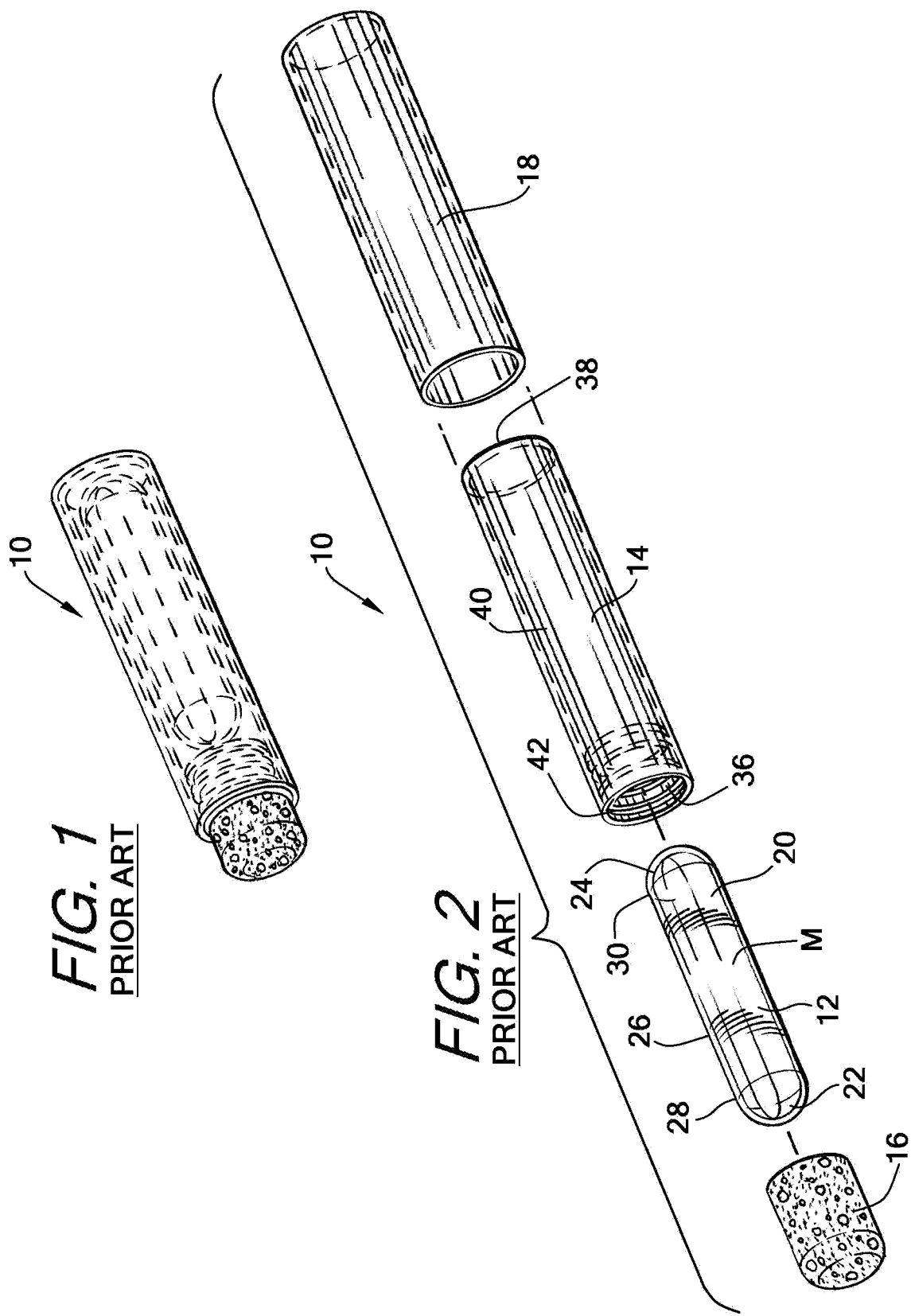

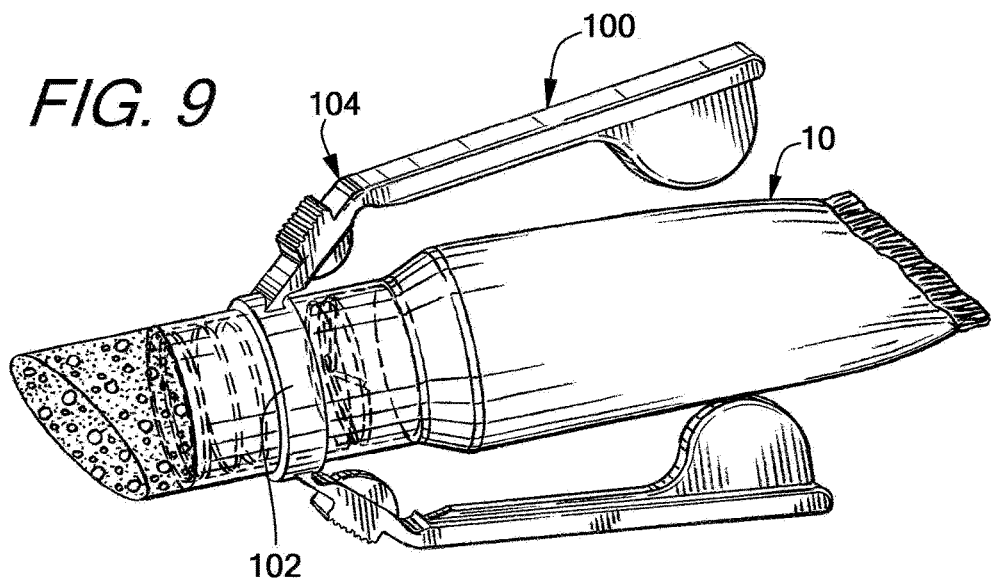
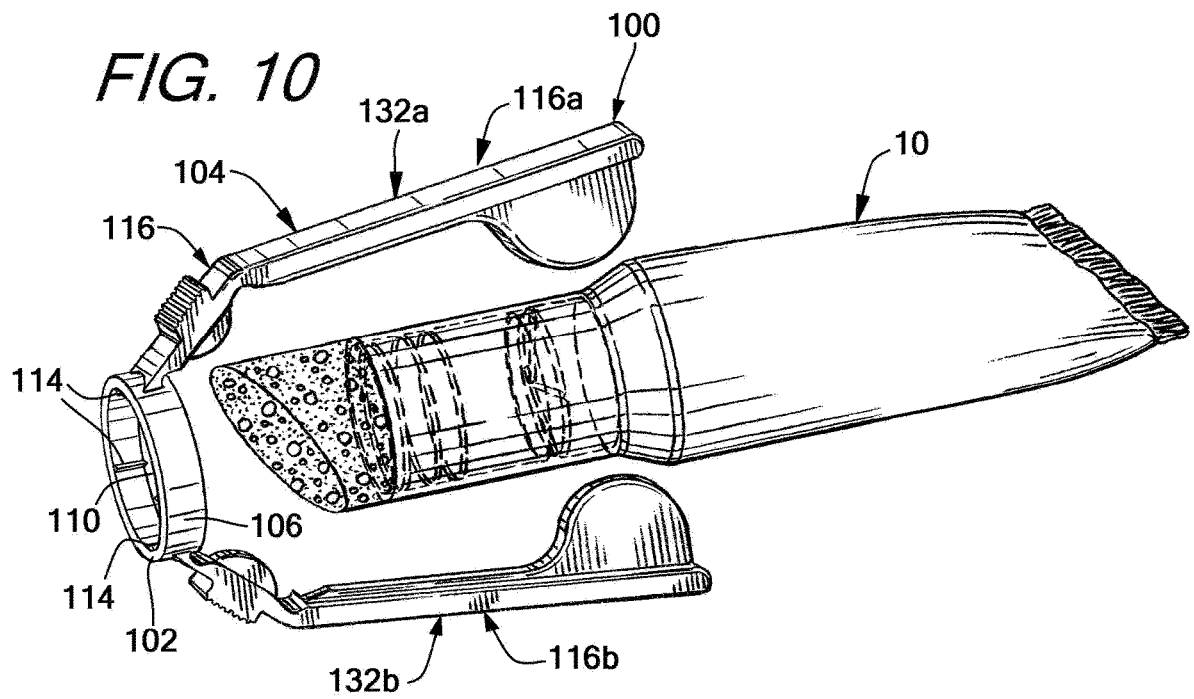

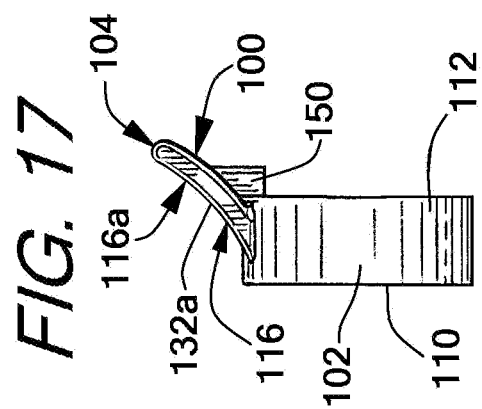
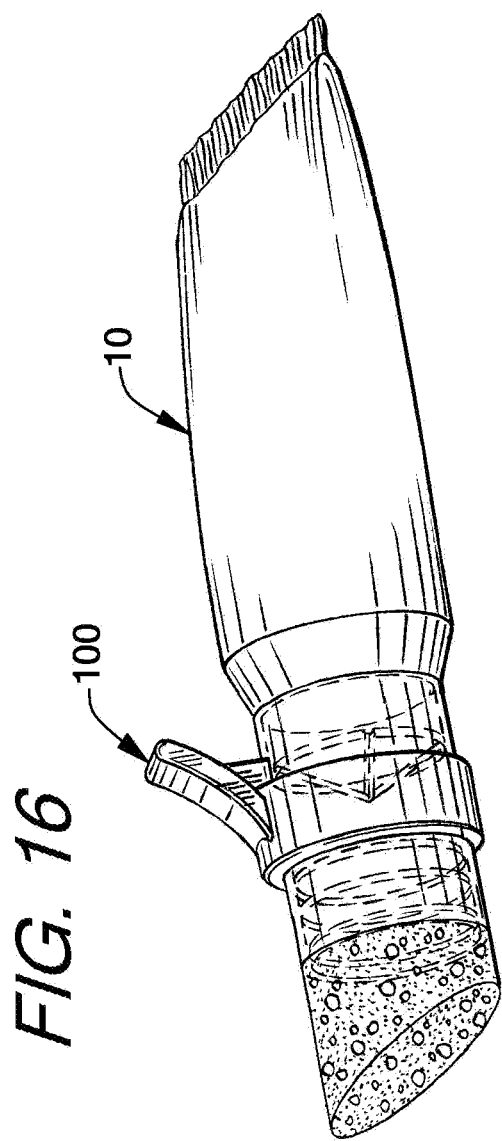
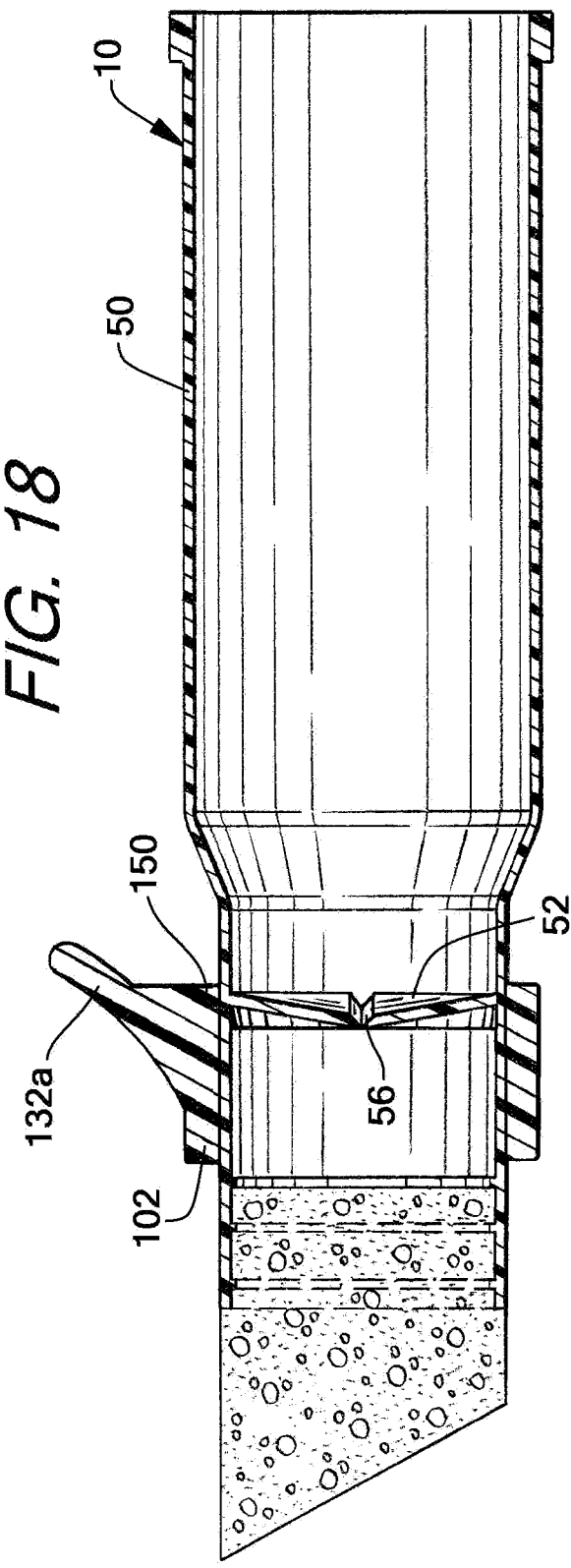

DISPENSER ACTUATOR ASSEMBLY

CROSS-REFERENCE TO RELATED APPLICATIONS

The present application claims the benefit of U.S. Patent Application No. 62/746,374, filed on Oct. 16, 2018, and this application is also a continuation-in-part application of and claims priority to U.S. patent application Ser. No. 15/681,973 filed on Aug. 21, 2017, now U.S. Pat. No. 10,669,065, U.S. patent application Ser. No. 15/681,992 filed on Aug. 21, 2017, now U.S. Pat. No. 10,689,152, and U.S. patent application Ser. No. 15/683,221 filed on Aug. 21, 2017, now U.S. Pat. No. 10,526,110, and U.S. patent application Ser. No. 15/683,523 filed on Aug. 21, 2017, now U.S. Pat. No. 10,518,930, which applications are incorporated by reference in their entireties herein and made a part hereof.

FEDERALLY SPONSORED RESEARCH OR DEVELOPMENT

None.

TECHNICAL FIELD

The invention relates generally to an actuator assembly for a dispenser and more particularly, to an dispenser actuator assembly having a base member configured to mount on a fracturable plastic ampoule assembly or a crushable glass ampoule assembly wherein a dispenser actuator assembly in the form of a first actuator arm and a second actuator arm are operably connected to the base member and dimensioned to rupture the plastic ampoule or glass ampoule assembly.

BACKGROUND OF THE INVENTION

Dispensers such as glass ampoule assemblies are well known in the art and are often designed to be single-use disposable dispensers. A glass ampoule assembly typically includes a rupturable or crushable container such as a glass ampoule that contains a flowable material to be dispensed. The glass ampoule is contained in an outer container that may be made from a plastic material and having an open end and a closed end. The glass ampoule assembly may further include an applicator such as a swab that fits in the open end of the outer container. The applicator assists in dispensing the flowable material after the glass ampoule is crushed. The glass ampoule assembly may also include a cover member such as a cardboard sleeve that is used when initially storing and transporting the glass ampoule assembly wherein the applicator end of the glass ampoule assembly is inserted into the cardboard sleeve. An opposite end of the glass ampoule assembly may be inserted into the cardboard sleeve wherein the applicator extends out of the sleeve. A user may squeeze the cardboard sleeve via finger pressure to deflect the plastic outer container and crush the glass ampoule wherein the flowable material is dispensed from the applicator. Plastic ampoules are also known in the art and having fracturable membranes. Certain embodiments of plastic ampoules have a fracturable membrane having a weld seam that fractures in response to force applied by a user proximate the membrane. Attempts have been made to design ampoule holders that assist in rupturing the ampoule. These designs, however, have been high in cost and cumbersome in design and operation. Furthermore, the glass ampoule is not ruptured in an optimum location wherein dispensing of the flowable material becomes problematic because of obstruction from fractured pieces of the glass ampoule.

Additional problems have also been experienced with the glass ampoule assemblies. In some instances, users do not have sufficient finger strength to rupture the glass ampoule. For example, users of advanced age oftentimes have arthritis and cannot rupture the glass ampoule. In other instances, upon rupturing the glass ampoule, glass shards puncture through the outer container and injure the user. In still other instances, the glass ampoule is typically ruptured at a central location of the glass ampoule. Rupturing the ampoule at the central location leaves a dome-shaped end portion of the glass ampoule intact. The dome-shaped end portion may end up positioned at the applicator wherein the flow of the flowable material is restricted from the dispenser. Furthermore, some actuator structures are integral with the overall dispenser assembly and do not provide an ability to be reused. Certain users have experienced difficulty in fracturing the weld seam of plastic ampoule assemblies such as when the users have limited finger strength due to certain conditions such as arthritis.

While glass ampoule assemblies, plastic ampoule assemblies and associated dispenser/ampoule holders/actuator assemblies according to the prior art provide a number of advantageous features, they nevertheless have certain limitations. The present invention seeks to overcome certain of these limitations and other drawbacks of the prior art, and to provide new features and new uses not heretofore available. A full discussion of the features and advantages of the present invention is deferred to the following detailed description, which proceeds with reference to the accompanying drawings.

SUMMARY OF THE INVENTION

The present invention provides a dispenser actuator assembly designed to actuate a dispenser to dispense a flowable material from the dispenser. It is understood that any of the exemplary embodiments of the dispenser actuator assemblies disclosed herein can be used to actuate a glass ampoule assembly or a plastic ampoule assembly as described herein.

According to a first aspect of the invention, a dispenser actuator assembly is provided for actuating a dispenser such as a glass ampoule assembly. The glass ampoule assembly has a rupturable glass ampoule containing a flowable material. The glass ampoule is contained within an outer container. The outer container has a first open end and a second closed end and the glass ampoule assembly has an applicator positioned in the first open end. The dispenser actuator assembly has a base member configured to mount on the outer container. An actuator assembly is operably connected to the base member wherein the actuator assembly has a first actuator arm and a second actuator arm each pivotally connected to the base member. The first actuator arm and the second actuator arm extend from the base member in generally opposed relation defining a first position. The first actuator arm has a first protrusion depending therefrom and the second actuator arm has a second protrusion depending therefrom. The first actuator arm and the second actuator arm are pivotable from the first position towards one another to a second position wherein the first protrusion is configured to engage the outer container and the second protrusion is configured to engage the outer container to rupture the glass ampoule wherein the flowable material is configured to be dispensed from the glass ampoule assembly.

According to another aspect of the invention, the dispenser can take the form of a plastic ampoule assembly. The plastic ampoule assembly has a fracturable membrane having a weld seam. The dispenser ampoule assembly is configured to be mounted on the plastic ampoule assembly wherein the weld seam is fractured by the dispenser actuator assembly to dispense flowable material from the dispenser.

According to a further aspect of the invention, a dispenser actuator assembly for actuating a dispenser for dispensing a flowable material is provided. The dispenser is in the form of a plastic ampoule assembly having a container having an outer wall and membrane collectively defining a first chamber containing the flowable material. The membrane has a thickness and a weld seam, the weld seam having a thickness less than the thickness of the membrane. The dispenser actuator assembly has a base member having an opening configured to mount on the container. A fracturing mechanism is operably connected to the base member. The fracturing mechanism has a first extending member and a second extending member. The first extending member and the second extending member are positioned on the base member in opposed relation to define a first neutral position. Each extending member has a projection positioned proximate the membrane when the base member is configured to be mounted on the container. In response to deflection of the extending members towards one another to an actuating position, the projections are configured to deflect the outer wall proximate the membrane wherein the weld seam is configured to fracture to create an opening through the membrane configured to allow the flowable material to pass therethrough and from the container.

According to a further aspect of the invention, the base member is an annular ring dimensioned to be configured to fit circumjacently around the outer container in an interference fit. In another exemplary embodiment, the base member is an annular ring that defines an inner surface. The inner surface has a plurality of ribs extending from the inner surface, the ribs configured to engage the outer container when the base member is mounted on the container. In a further exemplary embodiment, the opening of the base member extends completely through the base member.

According to another aspect of the invention, the projections are configured to be spaced from the outer wall of the container prior to deflection of the extending members. In additional exemplary embodiments, the projections depend from an underside of the extending members. The projections have a length configured to extend beyond the membrane when the base member is mounted on the container. In addition, the projections have a contoured surface wherein the contoured surface is configured to deflect the outer wall in response to the deflection of the extending members.

According to yet another aspect of the invention, the first extending member has a cut-out portion proximate an end of the first extending member extending from the base member. The cut-out portion defines a first hinge of the first extending member wherein the first extending member deflects about the first hinge. The second extending member has a cut-out portion proximate an end of the second extending member extending from the base member. The cut-out portion defines a first hinge of the second extending member wherein the second extending member deflects about the first hinge.

According to a further aspect of the invention, the extending members have a first segment and a second segment, the respective first segments projecting from the base member. The second segment has a rib depending from the second segment. The depending rib is configured to further deflect the outer wall of the container to force the flowable material through the membrane.

According to another aspect of the invention, an interface area is defined between the first segment and the second segment wherein the interface area has a second cut-out portion defining a second hinge wherein the second segment is configured to pivot about the second hinge towards the outer wall. In a further exemplary embodiment, the second cut-out portion is positioned on an exterior surface of the extending member.

According to another aspect of the invention, a dispenser actuator assembly for actuating a dispenser for dispensing a flowable material is provided. The dispenser is in the form of a plastic ampoule assembly having a container having an outer wall and membrane collectively defining a first chamber containing the flowable material. The membrane has a thickness and a weld seam, the weld seam having a thickness less than the thickness of the membrane. The dispenser actuator assembly has a base member having an opening configured to mount on the container. The dispenser actuator assembly also has a fracturing mechanism operably connected to the base member. The fracturing mechanism has a first extending member projecting from the base member, the first extending member having a first segment and a second segment. The first segment is connected to the base member and has a cut-out portion defining a first hinge allowing the first segment to pivot about the base member. The first segment has a first projection configured to be positioned proximate the membrane when the base member is mounted on the container. The first segment has a first position wherein the first projection is configured to be spaced from the outer wall. The second segment is connected to the first segment at a first interface area. The first interface area has a cut-out portion defining a second hinge allowing the second segment to pivot about the first segment. The second segment has a first depending rib. The fracturing mechanism also has a second extending member projecting from the base member, the second extending member positioned on the container generally in opposed relation to the first extending member. The second extending member has a first segment and a second segment. The first segment is connected to the base member and has a cut-out portion defining a third hinge allowing the first segment of the second extending member to pivot about the base member. The first segment of the second extending member has a second projection configured to be positioned proximate the membrane when the base member is mounted on the container. The first segment of the second extending member has a first position wherein the second projection is configured to be spaced from the outer wall. The second segment of the second extending member is connected to the first segment of the second extending member at a second interface area. The second interface area has a cut-out portion defining a fourth hinge allowing the second segment of the second extending member to pivot about the first segment of the second extending member. The second segment of the second extending member has a second depending rib. A porous member positioned in the opening defined by the second chamber. In response to a user deflecting the first segment of the first extending member and the first segment of the second extending member towards one another about the respective first hinge and second hinge to respective deflected positions, the first projection is configured to deflect the outer wall proximate the membrane and the second projection is configured to deflect the outer wall proximate the membrane wherein the weld seam is configured to fracture creating an opening through the membrane configured to allow the flowable material to pass from the first chamber, past the membrane, and into the second chamber, wherein the flowable material is configured to contact the porous member and be dispensed from the porous member. Also, in response to a user deflecting the second segment of the first extending member and the second segment of the second extending member about the respective third and fourth hinges to respective deflected positions, the first depending rib and the second depending rib are configured to deflect the outer wall proximate the first chamber to force further flowable material from the first chamber and into the second chamber to be dispensed from the porous member.

According to another aspect of the invention, a dispenser actuator assembly is provided for actuating a dispenser for dispensing a flowable material. The dispenser in the form of a plastic ampoule assembly having a container having an outer wall and membrane collectively defining a first chamber containing the flowable material. The membrane has a thickness and a weld seam, the weld seam having a thickness less than the thickness of the membrane. The dispenser actuator assembly has a base member having an opening configured to mount on the container. A fracturing mechanism is operably connected to the container. The fracturing mechanism has an extending member projecting from the base member. The extending member has a projection configured to be positioned proximate the membrane. In response to deflection of the extending member, the projection is configured to deflect the outer wall proximate the membrane wherein the weld seam is configured to fracture creating an opening through the membrane and configured to allow the flowable material to pass therethrough and from the dispenser.

According to a further aspect of the invention, the projection has a first end connected to the extending member and a second end connected to the base member. In a further exemplary embodiment, the projection depends from an underside of the extending member. The extending member covers the projection.

According to a further aspect of the invention, the projection has a length that is configured to extend beyond the membrane.

According to another aspect of the invention, the projection depends from an underside of the extending member. The projection has a distal end, wherein when the base member is configured to be connected to the container, no space is present between the distal end of the projection and the outer wall of the container.

According to yet another aspect of the invention, the extending member has a contoured surface. In other exemplary embodiments, the extending member has a concave outer surface. The extending member can be dimensioned to receive a thumb pad of a user.

According to a further aspect of the invention, the dispenser defines a longitudinal axis. The extending member has a first segment and a second segment connected to the first segment. The first segment extends from the outer wall, and the second segment extends from the first segment along an axis configured to be generally parallel to the longitudinal axis.

According to yet another aspect of the invention, the fracturing mechanism comprises a first fracturing mechanism and a second fracturing mechanism. The first fracturing mechanism and second fracturing mechanism are positioned on the base member in opposed relation.

According to another aspect of the invention, a dispenser actuator assembly is provided for actuating a dispenser for dispensing a flowable material. The dispenser is in the form of a plastic ampoule assembly having a container having an outer wall and membrane collectively defining a first chamber configured to contain the flowable material. The membrane has a thickness and a weld seam, the weld seam having a thickness less than the thickness of the membrane. The container defines a longitudinal axis. The dispenser actuator assembly has a base member having an opening configured to mount on the container. A fracturing mechanism is operably connected to the base member. The fracturing mechanism has a first extending member and a second extending member. The first extending member and the second extending member are positioned on the base member in spaced relation, wherein the first extending member and the second extending member are configured to extend above the longitudinal axis. In response to deflection of the extending members towards one another, the outer wall is configured to be deflected proximate the membrane wherein the weld seam is configured to be fractured creating an opening through the membrane configured to allow the flowable material to pass therethrough and from the dispenser.

According to a further aspect of the invention, the base member comprises a collar configured to be positioned on the outer wall of the container. The collar has a passageway between the first extending member and the second extending member, and the passageway is in communication with the opening. In a further exemplary embodiment, the extending members extend from the collar. The collar has a length configured to extend beyond the membrane when the base member is configured to be mounted on the container.

According to another aspect of the invention, the first extending member has a first segment and a second segment connected to the first segment of the first extending member, the first segment extending from the base member. The second segment extends from the first segment in a direction configured to be along an axis generally parallel to the longitudinal axis of the container.

According to a further aspect of the invention, the outer wall of the container is cylindrical and has a cylindrical contour. The collar is configured to be connected to the container along the cylindrical contour of the outer wall.

According to yet another aspect of the invention, the first extending member and the second extending member are configured to be positioned on the container in a radially spaced relation and at locations above the longitudinal axis of the container.

According to a further aspect of the invention, when the base member is configured to be mounted on the container, the first extending member is configured to be positioned at the outer wall at a first location and the weld seam extends to the outer wall at a second location. The second location is remote from the first location.

According to yet another aspect of the invention, a dispenser and actuator assembly are provided. The dispenser has a container having an outer wall and membrane collectively defining a first chamber configured to contain the flowable material. The membrane has a thickness and a weld seam, the weld seam having a thickness less than the thickness of the membrane. The container defines a longitudinal axis. The actuator assembly has a base member slidably mounted on the container, and a fracturing mechanism operably connected to the base member. The fracturing mechanism has a first extending member and a second extending member, the first extending member and the second extending member positioned on the base member in spaced relation. In response to deflection of the extending members towards one another, the outer wall deflects proximate the membrane wherein the weld seam fractures creating an opening through the membrane configured to allow the flowable material to pass therethrough and from the dispenser. A plane is defined through the longitudinal axis wherein the first extending member and the second extending member are remote from the plane.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is perspective view of a prior art dispenser in the form of a glass ampoule assembly;

FIG. 2 is an exploded perspective view of the glass ampoule assembly of FIG. 1

FIG. 9 is a perspective view of a dispenser actuator assembly according to another exemplary embodiment of the present invention, the dispenser actuator assembly mounted on a plastic ampoule assembly;

FIG. 10 is an exploded view of the dispenser actuator assembly and plastic ampoule assembly of the FIG. 9;

FIG. 16 is a perspective view of a dispenser actuator assembly according to another exemplary embodiment of the present invention, the dispenser actuator assembly mounted on a plastic ampoule assembly;

FIG. 17 is a side elevation view of the dispenser actuator assembly of FIG. 16;

FIG. 18 is a cross-sectional view of the dispenser actuator assembly mounted on the plastic ampoule assembly shown in FIG. 16;

DETAILED DESCRIPTION OF THE PREFERRED EMBODIMENT

Figure 3:
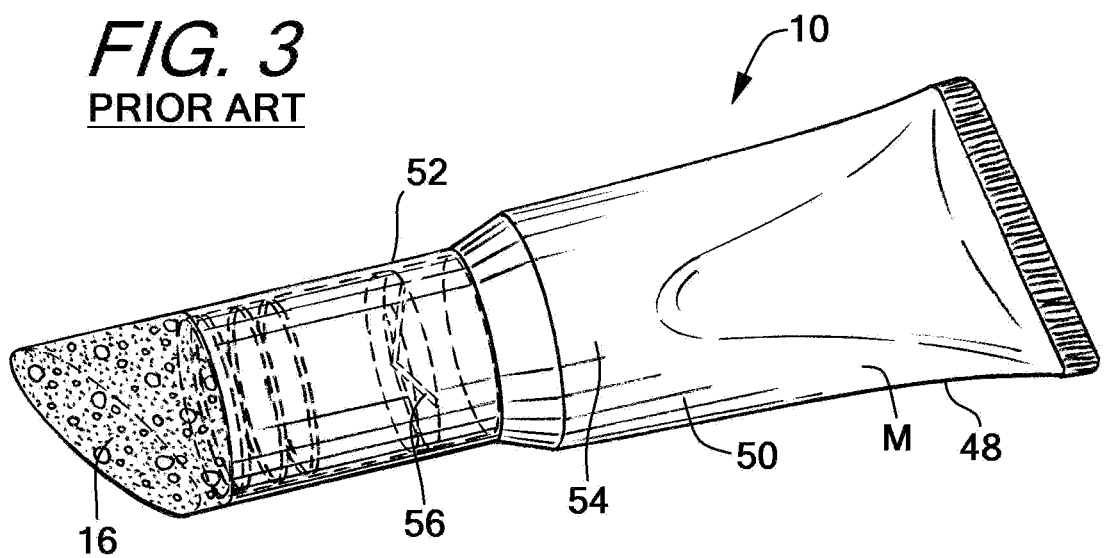
FIG. 3 is a perspective view of a prior art dispenser in the form of a plastic ampoule assembly.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention discloses a dispenser actuator assembly that can be used in conjunction with a dispenser to activate the dispenser and dispense flowable material from the dispenser. The dispenser actuator assembly may also be referred to as an ampoule actuator assembly or a dispenser holder or ampoule holder. The dispenser can take various forms and in certain exemplary embodiments, the dispenser may take the form of a glass ampoule assembly or a plastic ampoule assembly. The dispenser in the form of the glass ampoule assembly and a plastic ampoule assembly will be described followed by describing the dispenser actuator assembly including the connection of the components and actuating the dispenser.

FIGS. 1 and 2 disclose a dispenser used in accordance with an exemplary embodiment of the invention and generally designated with the reference numeral 10. The dispenser 10 generally includes a first container 12, a second container 14, or outer container 14, and an applicator assembly 16. A cover member 18 may optionally be utilized as explained in greater detail below. In this configuration, the dispenser 10 may also be referred to as a glass ampoule assembly 10. The glass ampoule assembly 10 generally has an elongated longitudinal axis. It is understood that the dispenser 10 or glass ampoule assembly 10 may take different forms as well such as other devices having rupturable containers.

FIGS. 1 and 2 show the first container 12. The first container 12 is generally structured to contain the flowable material M to be dispensed from the dispenser 10. The flowable material M is typically a liquid in an exemplary embodiment. It is understood, however, that flowable materials in other forms could be used such as gels or powders etc. The first container 12 defines a chamber 20 therein that contains the flowable material M. The first container 12 has a first end 22 that is closed and also has a second end 24 that is closed as well as an intermediate section 26 therebetween. The intermediate section 26 of the first container 12 is generally cylindrical in shape and has a generally circular cross-section. The first end 22 is generally dome-shaped and the second end 24 is generally dome-shaped. Other configurations are also possible. As further shown in FIGS. 1 and 2, a first interface area 28 is defined at or proximate the juncture between the first dome-shaped end 22 and an end of the intermediate section 26. Similarly, a second interface area 30 is defined at or proximate the juncture between the second dome-shaped end 24 and the other end of the intermediate section 26. Thus, the first interface area 28 is at the location of the first container 12 that transitions from an end of the intermediate section 26 to the dome shape of the first end 22. Similarly, the second interface area 30 is at the location of the first container 12 that transitions from an end of the intermediate section 26 to the dome shape of the second end 24. The first container 12 may be dimensioned to have a diameter and length to define the first chamber 20 in a size to contain a desired amount of the flowable material M. The first container 12 is designed to be fracturable, rupturable or crushable as described in greater detail below. In an exemplary embodiment, the first container 12 is made from a rigid fracturable material such as glass. The first container 12 may be a traditional glass ampoule. Glass ampoules are known in the art and provide a hermetically-sealed chamber for containing the flowable material M. In one exemplary embodiment, a single glass ampoule 12 is used. It is understood that the dispenser 10 could be configured to use multiple glass ampoules 12 as described in greater detail below.

FIGS. 1 and 2 further show the second container 14. The second container 14 may be referred to as an outer container 14. The second container 14 has an open first end 36 and a closed second end 38, and an outer wall 40 therebetween. The outer wall 40 of the second container 14 defines a second chamber 42. The second chamber 42 is cooperatively dimensioned and configured to receive at least a portion of the first container 12, and typically the entire first container 12 is received in the second container 14. Thus, in an exemplary embodiment, the second container 14 is generally cylindrical and receives the first container 12 in a generally snug-fit configuration. The second container 14 is made from a flexible resilient material such as plastic in an exemplary embodiment. The second container 14 may be transparent or translucent plastic wherein the flowable material M in the first container 12 can be visible through the second container 14 and also through the first container 12. The second container 14 may also be made from opaque material when the flowable material M or other contents are light sensitive.

FIGS. 1 and 2 further show the applicator 16 or applicator assembly 16. The applicator assembly 16 assists in dispensing the flowable material M from the dispenser 10 to a receiving surface. Any applicator assembly 16 that performs this function can be used in the dispenser 10. Thus, the applicator assembly 16 can take various forms including a swab assembly, a dropper assembly, a roller ball or a brush assembly. The swab applicator may also take various forms such as being made from absorbent, porous material, and that relies on a wicking action to dispense the flowable material M. It is also understood that the applicator assembly 16 may have a filter member operably associated therewith. The filter member is structured to allow passage of the flowable material M through the filter member while preventing passage of glass shards from the fractionated glass ampoule 12. The filter member may be positioned between the first end 22 of the first container 12 and the applicator assembly 16.

In one exemplary embodiment, the applicator assembly 16 is in the form of a swab assembly. The swab assembly can be made from material that promotes dispensing of the flowable material M through the swab assembly and onto a receiving surface. The applicator assembly 16 can also include other types of tips capable of applying flowable material onto a receiving surface.

In another exemplary embodiment, the applicator assembly 16 can be in the form of a dropper assembly. The applicator assembly 16 has a base having a protrusion extending therefrom at one end. The base has a dropper tip member extending from an opposite end. The applicator assembly 16 has a central conduit extending therethrough from a distal end of the protrusion to a distal end of the dropper tip member. The protrusion has a generally annular configuration and is dimensioned to be received by the open first end 36 of the second container 14. In an exemplary embodiment, the protrusion and the open first end 36 of the second container 14 are cooperatively dimensioned wherein the protrusion is received in the open first end 36 in an interference fit. As further described below, the applicator assembly 16 is configured to receive the flowable material M from the fractionated or crushed first container 12 and to dispense the flowable material M onto a receiving surface.

If desired, the dispenser 10 may also utilize the cover member (shown schematically), as is known the art. The cover member is designed to initially cover the applicator assembly 16 prior to activating the dispenser 10. The cover member 18 is dimensioned to fit snugly over the applicator assembly 16 and extend over a portion of the dispenser 10. One end of the cover member 18 may be closed although it is understood that both ends of the cover member 18 could be open ends. When preparing to activate the dispenser 10, the cover member 18 is removed from the dispenser 10. In certain prior art applications, an end of the dispenser 10 opposite of the applicator assembly 16 is inserted into the cover member 18. With the present invention as described in further detail below, the cover member 18 is not used during activation of the dispenser 10. The cover member 18 may be a cardboard or paper-based material in an exemplary embodiment. The cover member 18 could also be in the form of a cap the fits over the applicator assembly 16. It is also understood that the dispenser 10 can incorporate an identifying label.

To fabricate the dispenser 10, the first chamber 20 of the first container 12 is filled with a desired flowable material M. The open end of the first container 12 through which the flowable material passed to fill the first container 12 is sealed as is known in glass ampoule technology. A sealed glass ampoule 12 having the flowable material M therein is thereby provided. The filled first container 12 is then inserted through the open first end 36 and into the second chamber 42 of the second container 14. Preferably, the first container 12 is positioned in its entirety within the second chamber 42 of the second container 14. Once the first container 12 is positioned in the second container 14, the applicator assembly 16 is connected to the second container 14. If a filter member is desired, the filter member can be inserted into the open first end 36 of the second container 14 and adjacent one end of the first container 12. As can be appreciated from FIGS. 1 and 2, an end of the applicator assembly 16 is inserted into the open first end 36 of the second container 14.

It is understood that the dispenser 10 may utilize the cover member 18 in a single-use type container as described above and shown in FIGS. 1 and 2. The dispenser 10 may also eliminate the cover member 18 and be packaged in other outer packaging such as blister packaging.

It is understood that the dispenser actuator assembly can also be used with other types of dispensers 10 that utilize a rupturable feature in order to dispense flowable materials M from the dispenser 10. FIG. 3 shows another dispenser 10 in the form of a plastic ampoule 10. The plastic ampoule assembly has a container 48 having an outer wall 50 and a fracturable or rupturable membrane 52 defining a first chamber 54 for containing a flowable material M. The membrane 52 has a weld seam 56 formed during an injection molding process wherein a first segment of injected molding material abuts a second segment of injected molding material to form the weld seam 56 such as disclosed in U.S. Pat. Nos. 6,641,319 and 10,392,163, which patents are expressly incorporated by reference herein. As explained in greater detail below, force applied to the outer wall 50 proximate the membrane 52 fractures the weld seam 56 of the membrane 52 allowing flowable material in the chamber 54 to be dispensed from the dispenser 10. It is further understood that an applicator 16 is positioned in an open end defined by the outer wall 50 in a second chamber defined by the outer wall 50.

Thus, it is understood that the dispenser 10 can be a traditional glass ampoule assembly 10 or a plastic ampoule assembly 10. The dispenser 10 could further include other assemblies having rupturable of frangible structures that are capable of being actuated by the dispenser actuator assembly described herein. It is understood that the various exemplary embodiments of the dispenser actuator assembly disclosed herein can be used to actuate the glass ampoule assembly, the plastic ampoule assembly or other types of dispenser.

The present invention utilizes a dispenser actuator assembly generally designated with the reference numeral 100. The dispenser actuator assembly 100 may also be referred to as an ampoule actuator assembly 100 or dispenser/ampoule holder 100. As explained in greater detail below, the dispenser actuator assembly 100 cooperates with the dispenser 10 to actuate the dispenser 10. The structure of the dispenser actuator assembly 100 will first be described followed by a description of the cooperation and operation of the dispenser actuator assembly 100 with the dispenser 10. As discussed, it is understood that the dispenser actuator assembly 100 can be used with a plastic ampoule assembly 10 or a glass ampoule assembly 10. Many of the exemplary embodiments disclosed herein are shown being operably coupled to a plastic ampoule assembly 10, but it is understood the dispenser actuator assembly 10 can be modified in size to cooperate with a glass ampoule assembly 10.

The dispenser actuator assembly 100 generally includes a base member 102 and an actuator assembly 104. The actuator assembly 104 is operably connected to the base member 102 as further described below.

Figure 5:
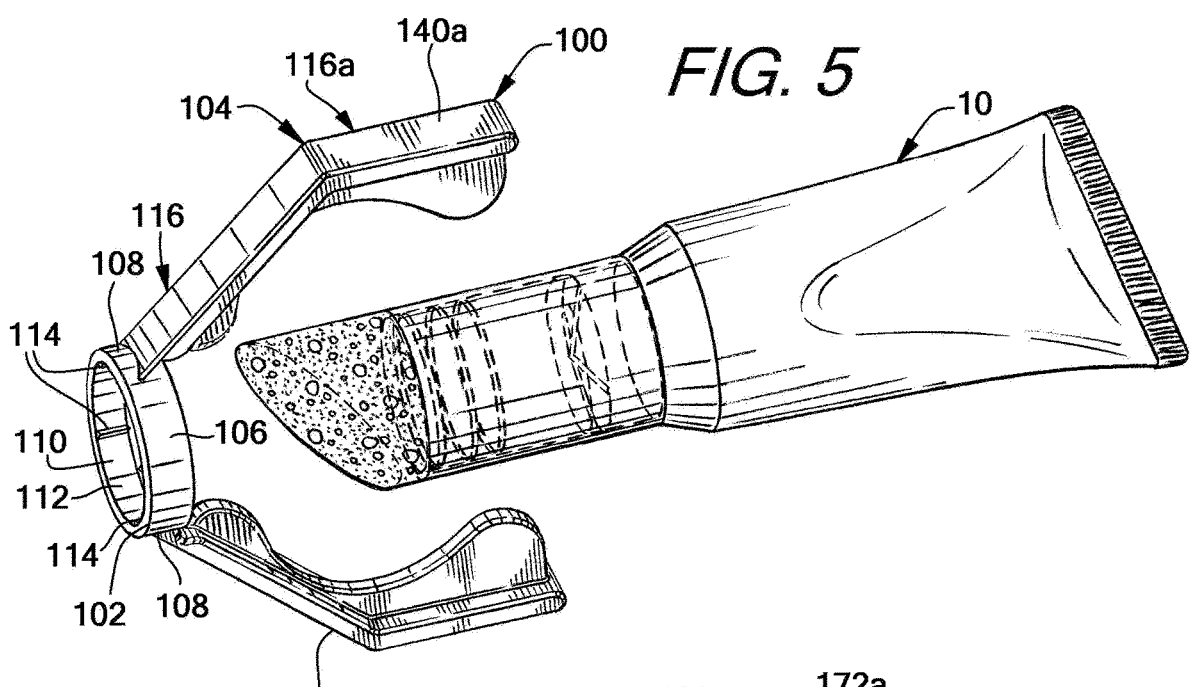
FIG. 5 is an exploded view of the dispenser actuator assembly and plastic ampoule assembly of the FIG. 4.
Figure 6:
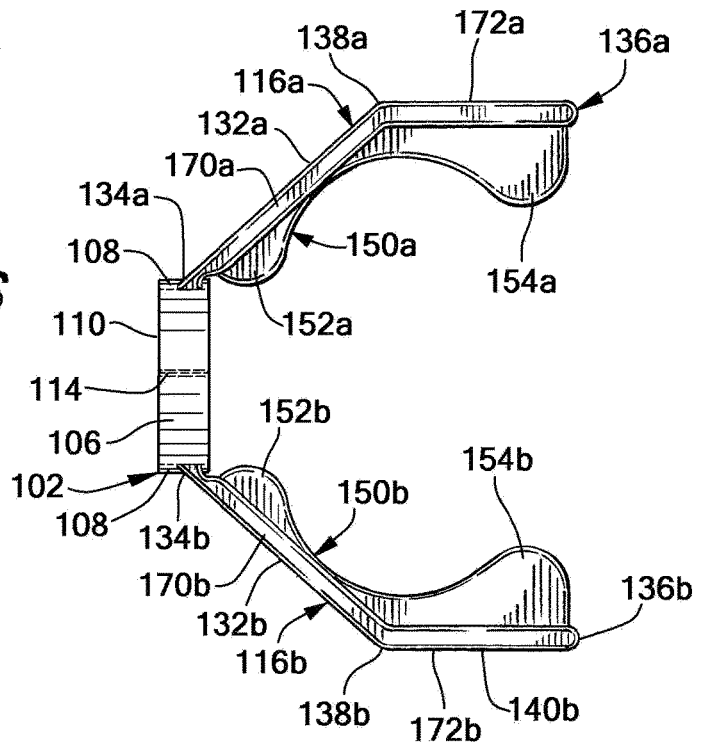
FIG. 6 is a side elevation view of the dispenser actuator assembly of FIG. 4.
Figure 7:
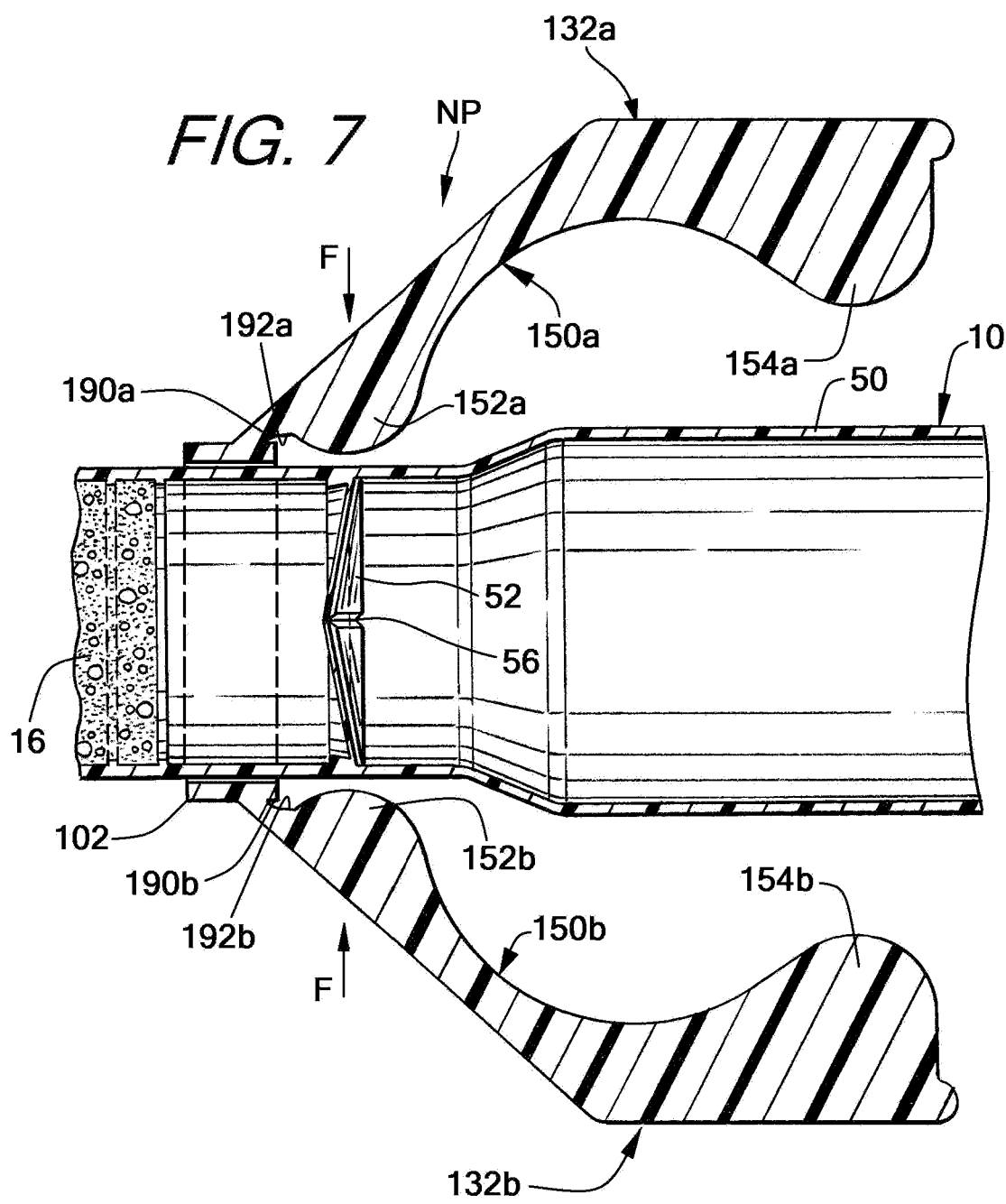
FIG. 7 is a cross-sectional view of the dispenser actuator assembly mounted on the plastic ampoule assembly shown in FIG. 4.

FIGS. 5-7 show the base member 102 of the dispenser actuator assembly 100. The base member 102 is generally a rounded member that fits around at least a portion of the plastic ampoule assembly 10. The base member 102 is further an annular member that in one exemplary embodiment is dimensioned to fit over the dispenser or plastic or glass ampoule assembly as described in greater detail below.

The base member 102 generally includes an annular ring member 106 and connection locations 108 for cooperation with the actuator assembly 104. The annular ring member 106 is a full ring member in an exemplary embodiment that defines an opening 110 therethrough to receive the dispenser as explained in greater detail below. Thus, in an exemplary embodiment, the annular ring member 106 is dimensioned to fit circumjacently around the outer wall 50 of the plastic ampoule assembly 10 in an interference fit or circumjacently around the glass ampoule assembly 10 and, in particular, the second container 14 in an interference fit. It is understood that in other exemplary embodiments, the ring member 106 may not be a full ring member and have an interruption, slot or break in the member. The annular ring member 106 has an inner surface 112 that defines the opening 110. The inner surface 112 has a plurality of ribs 114 extending radially inwardly into the opening 110. In an exemplary embodiment, the ribs 114 extend axially or longitudinally along the inner surface 112 of the annular ring member 106. Furthermore, four ribs 114 are utilized and are spaced circumferentially on the inner surface 112 at 12 o'clock, 3 o'clock, 6 o'clock and 9 o'clock positions. It is further understood that a single rib 114 could be employed or other numbers of ribs 114. The ribs 114 could also take the form of ribs extending circumferentially along the inner surface 112 of the annular ring member 106. The ribs 114 assist in providing an interference fit with the outer wall 50 of the plastic ampoule assembly 10 or the second container 14 of the glass ampoule assembly 10 when the base member 102 is mounted on the second container 14. The annular ring member 106 may have a flange extending circumferentially around the ring member 106 at a proximate end of the ring member 106. The flange would assist in adding rigidity and strength to the proximal end of the base member 102. The added rigidity and strength provided by the flange also helps when ejector pins push the base member 102 off of the mold member during the injection molding process.

FIGS. 5-7 further show the connection locations 108 of the base member 102. The connection locations 108 are generally locations where the actuator assembly 104 connects to base member 102 or where the actuator assembly 104 extends from the base member 102. The connection locations 108 can vary on the base member 102 in other exemplary embodiments.

As shown in FIGS. 5-7, the base member 102 is formed as a full annular ring member in one exemplary embodiment. The base member 102 is designed to receive or hold the dispenser 10 or plastic or glass ampoule assembly 10, and it is understood that the base member 102 may not have a full ring-shaped configuration. For example, the base member 102 can have certain segments eliminated and not utilized while still having a configuration to receive or hold the glass ampoule assembly 10. The base member 102 could have a slot formed therein to define separate segments that may be resiliently flexible. The base member 102 further defines the annular ring member 106 that defines the opening 110 for the glass ampoule assembly 10. It is understood that the inner surface of the base member 102 could be tapered such that the entry of the base member 102 is slightly larger at one end. In a particular exemplary embodiment, the base member 102 tapers to a larger dimension towards the actuator arms of the actuator assembly 104. This provides for easier insertion of the glass ampoule assembly 10 or plastic ampoule assembly 10 at that end. In one exemplary embodiment, there is a 2-degree taper. In other exemplary embodiments, the taper could be 1-3 degrees. It is further understood that the taper can be in an opposite direction as well. The outer container 14 of the glass ampoule assembly 10 may have a rounded end that also assists insertion/mounting between the dispenser actuator assembly 100 and the glass ampoule assembly 10. The outer wall 50 of the plastic ampoule assembly 10 could also have a rounded end or taper to assist in the base member 102 fitting over the outer wall 50.

FIGS. 5-7 further show the actuator assembly 104 of the dispenser actuator assembly 100. In one exemplary embodiment, the actuator assembly 104 has a first fracturing mechanism 116a and a second fracturing mechanism 116b. The fracturing mechanisms 116a,116b of the actuator assembly 104 generally includes a first actuator arm 132a and a second actuator arm 132b. The first actuator arm 132a may be considered a first extending member 132a and the second actuator arm 132b may be considered a second extending member 132b, which nomenclature can apply to further embodiments described herein. The first extending member 132a may also be considered to have a first segment 170a and a second segment 172a. Similarly, the second extending member 132b may be considered to have a first segment 170b and a second segment 172b. It is understood that the first actuator arm 132a and the second actuator arm 132b are generally symmetrical and have similar structural features. As explained in greater detail below, the first actuator arm 132a and the second actuator arm 132b are connected to the base member 102 at the connection locations 108. It is understood that additional intermediate structures could be used between the base member 102 and the actuator arms 132a,132b. It is understood that the first actuator arm 132a and the second actuator arm 132b are similar in structure and positioned generally symmetrically as described in greater detail below. It is also understood that description regarding the first actuator arm 132a will generally apply to the second actuator arm 132b. The structures of the first actuator arm 132a are referenced with an "a" designation while the structures of the second actuator arm 132b are referenced with a "b" designation.

FIGS. 5-7 further show the first actuator arm 132a. The first actuator arm 132a has a proximal end 134a, a distal end 136a and an intermediate segment 138a. The intermediate segment 138a is considered to have the first segment 170a and the second segment 172a. The proximal end 134a is connected to the base member 102 and extends at an angle from the base member 102, e.g., the first segment 170a extends from the base member 102 at an angle. The proximal end 134a is connected to the base member 102 at the connection location 108. The intermediate segment 138a defines a floor segment 140a. The floor segment 140a may have a generally planar surface. The floor segment 140a may further have a finger pad in the form of a plurality of raised ridges. The floor segment 140a may provide for a tactile feel for the user for more proper finger/digit placement, as well as helping to maintain engagement of the fingers/digits with the actuator arms 132a,132b. The second segment 172a extends from the first segment 170a in a direction generally parallel to a longitudinal axis of the plastic ampoule assembly 10.

The first actuator arm 132a further has a depending protrusion 150a, or depending projection 150a, positioned on an underside of the first actuator arm 132a. The depending protrusion 150a has a first segment 152a and a second segment 154a. The first segment 152a has a contoured configuration and is configured to engage the outer wall 50 of the plastic ampoule assembly 10 and fracture the weld seam 56 of the membrane 54. The second segment 154a also has a contoured configuration. The shape of the second segment 154a allows the second segment 154a to manipulate the plastic ampoule assembly 10 or the glass ampoule assembly 10 to provide an enhanced pumping action to expel more fully the flowable material M from the assembly 10. In embodiments disclosed herein, the second segment 154a of the depending protrusion 150 may be considered a depending rib 154a. As further shown in FIGS. 6-7, the first actuator arm 132a has a first hinge 190a positioned at the proximal end 134a of the first actuator arm 132a. The first hinge 190a is defined by a cut-out portion 192a defined in the first actuator arm 132a. The first hinge 190a assists in the pivoting of the first actuator arm 132a as described in greater detail below. As discussed, the above description of the structure of the first actuator arm 132a is applicable for the structure of the second actuator arm 132b and having "b" designations.

The dispenser actuator assembly 100 is used with a dispenser 10 such as the plastic ampoule assembly 10 wherein the dispenser actuator assembly 100 is slid over the outer wall 50 of the plastic ampoule assembly 10 in a frictional interference fit. The longitudinal ribs 114 may engage the outer wall 50 of the container 48. When positioned on the outer wall 50 of the plastic ampoule assembly 10, the first segment 152a of the protrusion 150a is positioned proximate the membrane 52 and may be spaced from the outer wall 50 in a first neutral position. The dispenser actuator assembly 10 can also be used with the dispenser 10 being in the form of the glass ampoule assembly 10 to rupture the glass ampoule assembly 10 and dispense flowable material from the glass ampoule assembly 10. The glass ampoule assembly 10 is prepared such as by removing a cardboard sleeve if the sleeve is being used or removing the glass ampoule assembly 10 from any blister packaging. Alternatively, the glass ampoule assembly 10 may use the cover member 18 which is removed in preparation for dispensing flowable material from the glass ampoule assembly 10. The glass ampoule assembly 10 is inserted into the base member 102. The opening 110 defined by the base member 102 receives the glass ampoule assembly 10 wherein the base member 102 slides onto the second container 14. In one exemplary embodiment, the base member 102 slides onto the second container 14 in a frictional interference fit. The ribs 114 assist in engaging the outer surface of the outer container 14 of the glass ampoule assembly 10 to achieve a snug interference fit. In one exemplary embodiment, the glass ampoule assembly 10 is inserted into a distal end of the base member 102. Even if the taper is such that the distal end of the base member 102 is more narrow, the outer container 14 of the glass ampoule assembly 10 has a rounded edge that assists in smooth insertion/mounting. It is also understood that the dispenser actuator assembly 100 could also be slid over the glass ampoule assembly 10 at the proximal end of the base member 102. When the dispenser actuator assembly 100 is properly located on the glass ampoule assembly, the first depending protrusion 150a or projection 150a and the second depending protrusion 150b or projection 150b are positioned proximate the first interface area 28 of the glass ampoule 12. In addition, the first actuator arm 132*a* and the second actuator arm 132*b* extend towards the closed end 38 of the second container 14 of the glass ampoule assembly 10. The arms 132*a*,132*b* also extend towards a closed distal end of the container 48 of the plastic ampoule assembly 10.

It is understood that the one of the dispenser actuator assembly 100 and the plastic ampoule assembly 10 or the glass ampoule assembly 10 could have a locating structure thereon to properly position the dispenser actuator assembly 100 on the glass ampoule assembly 10 so that the actuator arms 132*a*,132*b* are properly positioned to rupture the glass ampoule 12. The location structure can also take the form of a cooperative structure on one of or both of the dispenser actuator assembly 100 and the glass ampoule assembly 10. For example, the outer wall 50 of the plastic ampoule assembly 10 or the second container 14 of the glass ampoule assembly 10 could have an annular, radially-inwardly formed indentation that the base member 102 is received therein to automatically locate the dispenser actuator assembly 100 on the proper location on the glass ampoule assembly 10. Similarly, an outwardly extending protrusion could be located on the second container wherein the base member 102 slides over the protrusion until the actuator assembly 100 fits adjacent the protrusion to be properly located. Multiple protrusions could also be used such as outwardly extending spaced protrusions wherein the actuator assembly 100 fits within spaced protrusions to be properly located.

Figure 4:
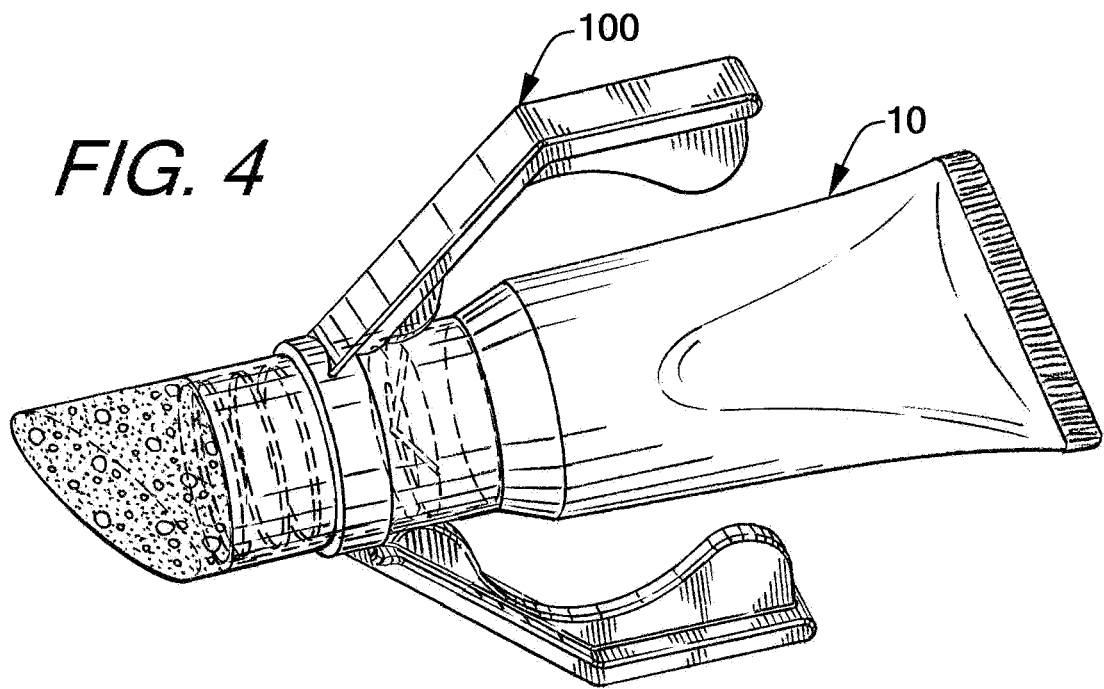
FIG. 4 is a perspective view of a dispenser actuator assembly according to an exemplary embodiment of the present invention, the dispenser actuator assembly mounted on a plastic ampoule assembly.

FIGS. 4 and 7 show the dispenser actuator assembly 100 positioned on and operably connected to the plastic ampoule assembly 10. The plastic ampoule assembly 10 is now ready to be actuated. The first actuator arm 132*a* and the second actuator arm 132*b* are in a first neutral position. The first container 12, or glass ampoule 12, is in a position to be ruptured wherein the flowable material M can be dispensed from the assembly 10. As further shown, the first depending protrusion or projection 150*a* of the first actuator arm 132*a* and the second depending protrusion or projection 150*b* of the second actuator arm 132*b* are spaced from the outer wall 50 and positioned over and proximate the membrane 52. Thus, a gap or space is initially maintained between the protrusions 150*a*,150*b* and the outer wall 50.

As can be appreciated from the figures, a user holds the dispenser actuator assembly 100 wherein a forefinger wraps around an underside of the base member 102 and engages the second actuator arm 132*b*. A thumb of the user engages the first actuator arm 132*a*. In particular, a user's forefinger and thumb engage the respective actuator arms 132*a*,132*b*. The user squeezes the actuator assembly 100 thereby applying a compressive force F (FIG. 7) to the first actuator arm 132*a* and the second actuator arm 132*b*. Other user digits could be used if desired. In response to this compressive force, the depending protrusion 150*a* of the first actuator arm 132*a* is deflected towards and engages the outer wall 50 and the depending protrusion 150*b* of the second actuator arm 132*b* is deflected towards and engages an opposite side of the outer wall 50 to an actuating position. As the user continues to depress the first actuator arm 132*a* and the second actuator arm 132*b*, the depending protrusion 150*a* of the first actuator arm 132*a* deflects the outer wall 50 wherein the weld seam 56 of the membrane 52 fractures. It is understood that the first hinges 190*a*,190*b* assist in the pivoting motion of the first and second actuator arms 132*a*, 132*b* about the base member 102. In a glass ampoule assembly, and appreciated from the figures discussed above, it is understood that the outer container 14 is deflected by the protrusions 150*a*,150*b* of the actuator arms 132*a*,132*b* to then engage the first interface area 28 of the glass ampoule 12. The midportions of the first segments 152*a*,152*b* assist in concentrating the force F onto the outer wall 50 proximate the membrane 52. It is further understood that the actuator arms 132*a*,132*b* themselves do not generally bend or flex as the arms 132*a*,132*b* are more rigid, but the arms 132*a*,132*b* flex or pivot. Upon rupture, the flowable material M passes from through the membrane 52 and into the applicator 16 and then dispensed from the plastic ampoule assembly 10. In a glass ampoule assembly, because force F is applied to the glass ampoule 12 at the first interface area 28, the domed portion of the glass ampoule 12 breaks into multiple pieces allowing enhanced flow of the flowable material M out of the glass ampoule 12 and into the second container 14 and to the applicator assembly 16. It has been determined by the inventors that if the glass ampoule 12 is ruptured at the interface area, the domed-section will break into multiple pieces rather than remaining intact while breaking away from the intermediate section of the glass ampoule 12. The flowable material M passes from the second container 14 and into the applicator assembly 16.

Figure 8:
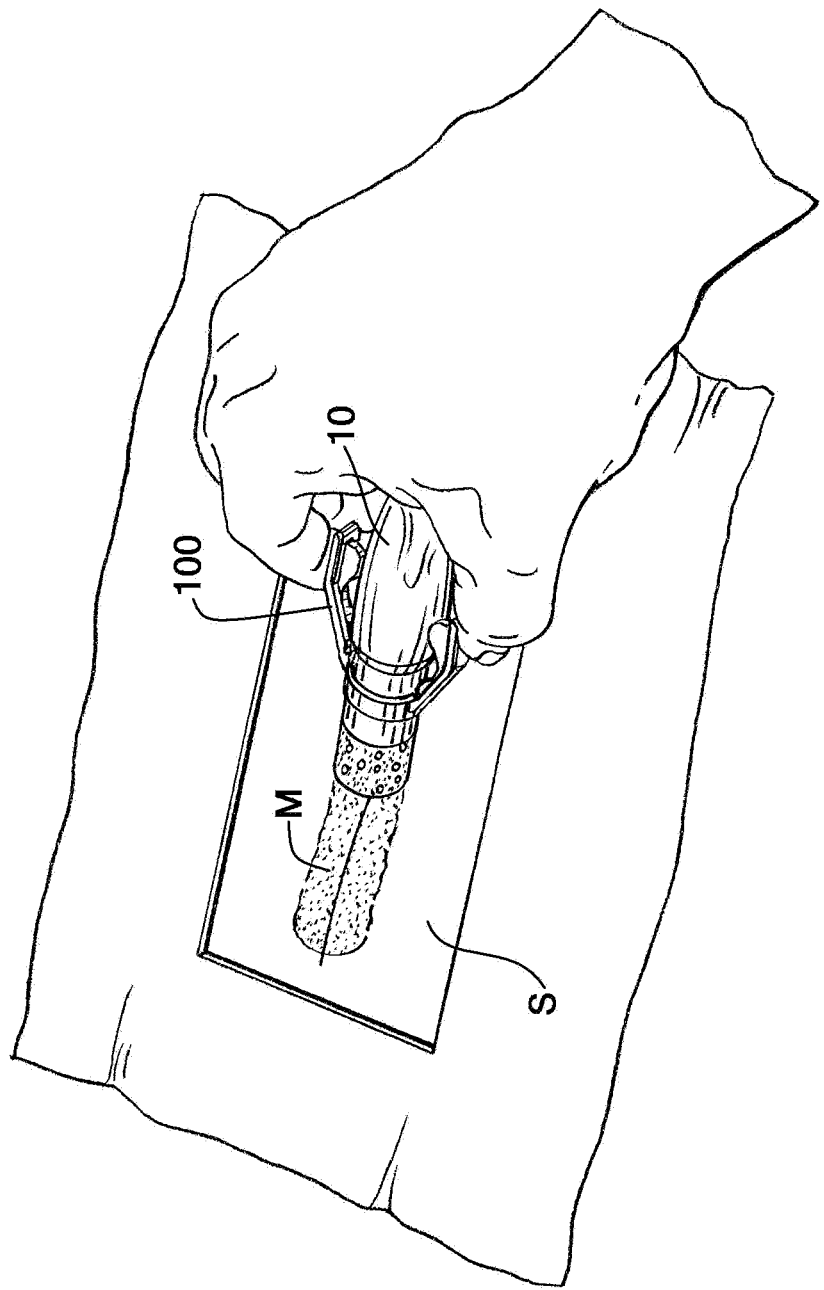
FIG. 8 is a perspective view a user dispensing flowable material onto a receiving surface.
Figure 11:
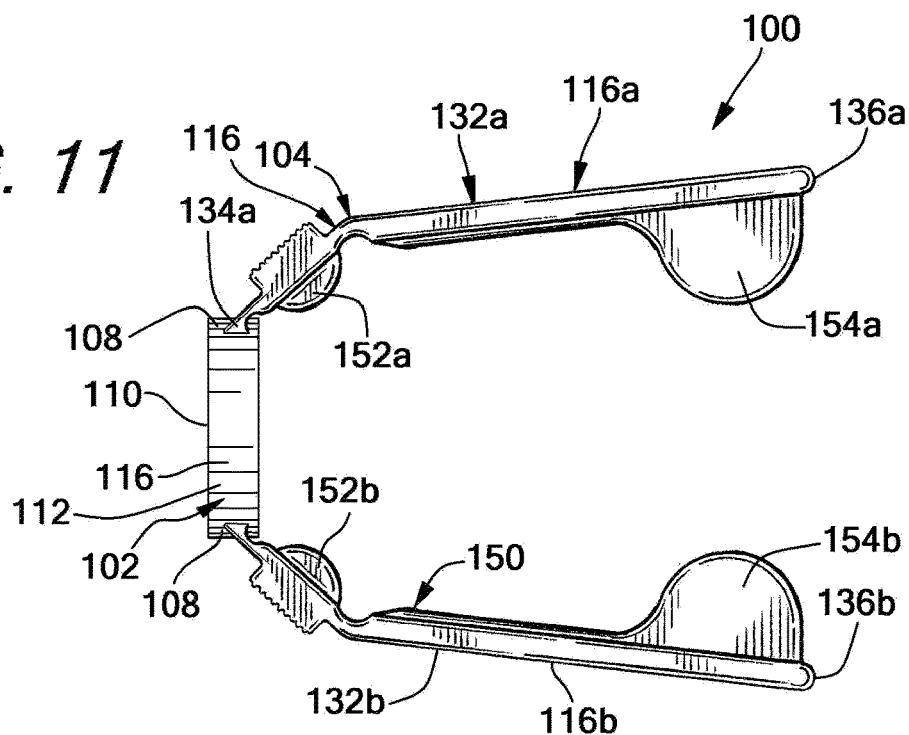
FIG. 11 is a side elevation view of the dispenser actuator assembly of FIG. 9.

As further can be appreciated from the figures, the user can continue to squeeze the actuator assembly 100 wherein the user engages the first actuator arm 132*a* and the second actuator arm 132*b* thereby continuing to apply the compressive force F wherein the depending protrusions 150*a*,150*b* are further deflected towards and engage the second container 14. As the user continues to depress first and second actuator arms 132*a*,132*b*, the respective second segments 154*a*,154*b* of the protrusions 150*a*,150*b* (the depending ribs 154*a*,154*b*) deflect the outer wall 50 to force flowable material M from the plastic ampoule assembly 10. Upon this additional movement, the flowable material M more easily passes from the plastic ampoule assembly 10. As shown in FIG. 8, the user can continue to depress the first and second actuator arms 132*a*,132*b* to dispense flowable material M onto a receiving surface S. For a glass ampoule assembly 10, because force F is applied to the glass ampoule 12 at the second interface area 30, the domed portion of the glass ampoule 12 breaks into multiple pieces allowing enhanced flow of the flowable material M out of the glass ampoule 12 and into the second container 14 and to the applicator assembly 16. It is further understood that the user can use the actuator arms 132*a*,132*b* and second segments 154*a*,154*b*, or depending ribs 154*a*,154*b*, to further deflect and manipulate the outer wall of the outer container 14 and force the flowable material M through the applicator assembly 16 and, therefore, to enhance dispensing of the flowable material M from the glass ampoule assembly 10.

In a glass ampoule assembly, it is understood that the applicator assembly 16 assists in minimizing the chance of glass shards from the ruptured glass ampoule 12 from passing out of the glass ampoule assembly 10. In addition, the outer wall of the second container 14 prevents glass shards from cutting fingers of the user thereby protecting the user's fingers from injury by the fractionated glass shards of the glass ampoule 12 that remain in the second container 14. Because a user engages the actuator assembly 100 to rupture the glass ampoule assembly 10 rather than engaging the glass ampoule assembly 10 directly, the chance of cutting a user's fingers/thumb from glass shards is further minimized. It is understood that additional structures could be incorporated into the glass ampoule assembly 10 such as filter assemblies to minimize the chance of glass shards from passing through the applicator assembly. The flowable material M can be dispensed from the glass ampoule assembly 10 and onto a receiving surface S. The receiving surface S can vary depending the particular type of flowable material M being dispensed.

As further appreciated from the figures, the user dispenses the flowable material M from the dispenser 10 with the aid of the dispenser actuator assembly 100. Once the flowable material M is emptied from the dispenser 10, the dispenser actuator assembly 100 can be removed from the dispenser 10. In this fashion, the dispenser actuator assembly 100 can be reused with multiple dispenser assemblies 10 or plastic or glass ampoule assemblies 10. In this configuration, the dispenser actuator assembly 100 can be formed from a more robust and higher-cost material. In other configurations, the material used to form the dispenser actuator assembly 100 could be a lower cost material that is designed as a one-time use wherein the dispenser actuator assembly 100 is disposable. In such case, the location structured used to position the dispenser actuator assembly 100 on the dispenser 10 could be structured to permanently attach the dispenser actuator assembly 100 to the glass ampoule assembly 10. Once the flowable material M is fully dispensed from the dispenser 10, the attached structures can be simply discarded together.

It is understood that the dispenser actuator assembly 100 can be formed in an injection molding process to form a unitary one-piece member. A wide variety of materials can be used to form the dispenser actuator assembly 100 wherein the actuator arms 132a,132b are resiliently flexible to actuate the glass ampoule assembly and then be reused on additional glass ampoule assemblies or plastic ampoule assemblies. In an exemplary embodiment, the dispenser actuator assembly is made from one of the polyolefin family of resins.

In another exemplary embodiment and described in an alternative fashion, the dispenser actuator assembly 100 has a base and a fracturing mechanism. The fracturing mechanism 116 includes a first fracturing mechanism 116a and a second fracturing mechanism 116b. The first fracturing mechanism 116a cooperates with the base member 102 at the connection location 108 of the base member 102, and has a first extending member and a first projection. The second fracturing mechanism 116b cooperates with the base member 102 at the connection location 108 of the base member 102, and has a second extending member and a second projection. As further appreciated, the fracturing mechanisms 116a,116b may also use a second projection on each extending member in the form of the depending rib. The components of the first fracturing mechanism 116a and the second fracturing mechanism 116b are generally symmetrical and similar in structure.

Also described in an alternative fashion and appreciated from FIGS. 4-7, a first hinge is defined in an underside of the first segment of the actuator arm 132a,132b. The first hinge 190a,190b is positioned generally adjacent the base member 102 and adjacent the first segment 152a,152b. The first hinge 190a,190b is positioned generally between the base member 102 and the first projection 150a,150b. The first hinge 190a,190b assists in activating the dispenser 10 as further described below. The first hinge 190a,190b is defined by a cut-out portion 192a,192b generally proximate an end of the first segment of the first extending member. In an exemplary embodiment as shown, the cut-out portion 192a,192b may be in the form of a notched structure including a generally v-shaped notch. Other structures are possible such as a more cut-out portion defining a more contoured inner surface. Additional hinge structures will be described below. As discussed, the first hinge 190a of the first extending member and the first hinge 190b of the second extending member are similar in structure and this description applies to the first hinge 190b of the second extending member. In an alternative embodiment, the first hinge could be positioned on an outer surface of the first segment. The first hinge could also be formed from cut-out portions in an outer surface and an underside surface of the first segment. The first hinge 190a,190b provides for enhanced pivoting of the first extending member and the second extending member.

As further appreciated from the figures and an alternate description, the second segment has a first depending rib 154a that extends from an inside surface of the second segment 172a. The first depending rib 154a has a contoured surface and a greater length towards the distal end of the second segment. The first depending rib 154a cooperates with the outer wall 50 of the container 48 during activation as will be described in greater detail below. As can be appreciated from the figures, the contoured surface of the first depending rib 154a may gradually meet with an additional intermediate contoured surface that joins with the contoured surface of the first projection. As explained in greater detail herein, the depending ribs can have varying alternative structures as desired to enhance operability of the dispenser 10. For example, the depending ribs could have a greater amount of material that depends at proximate a distal end of the ribs wherein the ribs taper towards their respective first segments of the extending members.

As further can be appreciated from the figures, the first fracturing mechanism 116a is positioned proximate the membrane 52 and at a first position on the container 48. The second fracturing mechanism 116b is positioned proximate the membrane 52 and at a second location on the container. In an exemplary embodiment, the second fracturing mechanism 116b is positioned generally opposite the first fracturing mechanism 116a. The first fracturing mechanism 116a is positioned generally 180° from the second fracturing mechanism 116b. The first fracturing mechanism 116a and the second fracturing mechanism 116b may also be positioned and spaced at other radial locations about the container.

Figure 12:
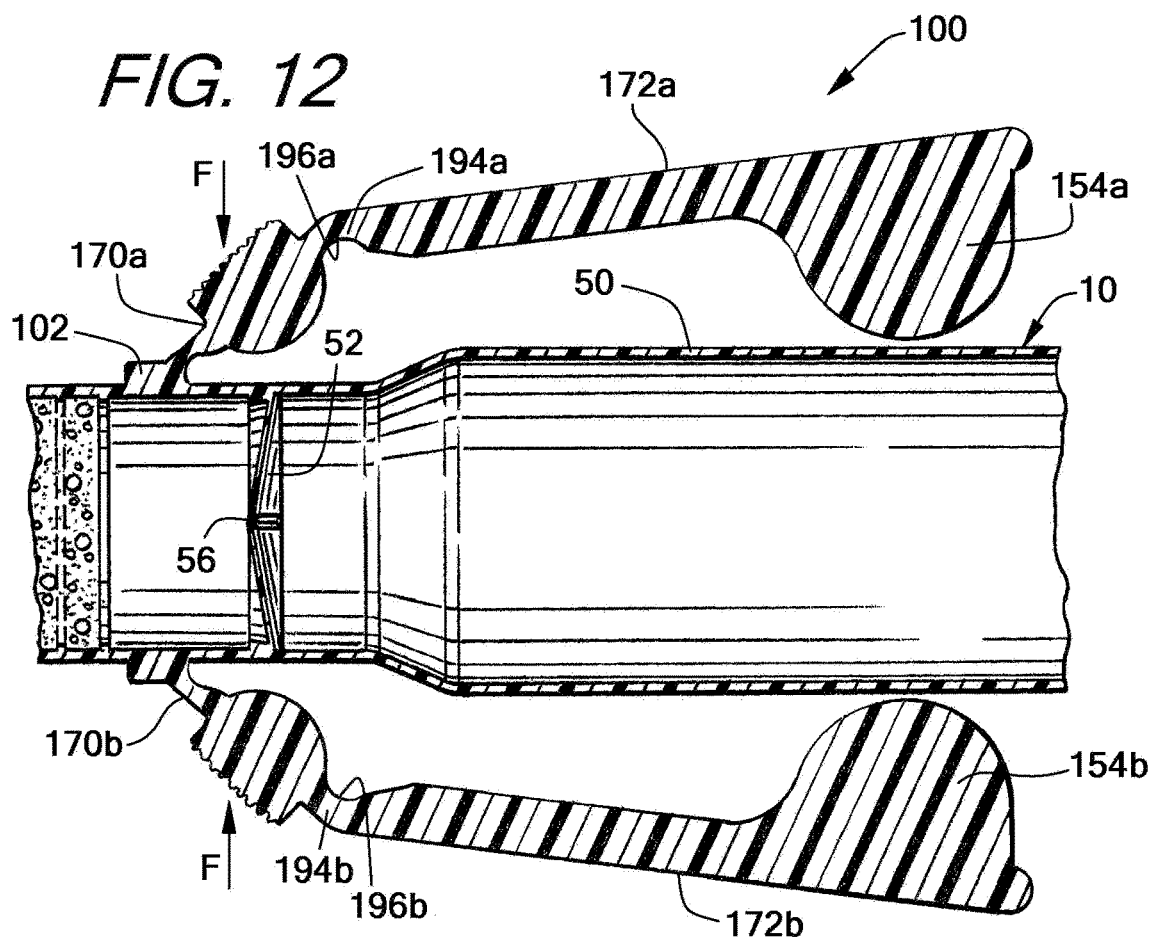
FIG. 12 is a cross-sectional view of the dispenser actuator assembly mounted on the plastic ampoule assembly shown in FIG. 9.

FIGS. 9-12 disclose another exemplary embodiment of the dispenser actuator assembly 100 of the present invention. Similar to the embodiment above, the dispenser actuator assembly 100 generally includes a base member 102 and an actuator assembly 104. The structures of the embodiment of FIGS. 9-12 are similar to the structures described in FIGS. 4-7 and are equally applicable to the embodiment of FIGS. 9-12. The base member 102 is similar in construction to the base member 102 of FIGS. 4-7. The actuator assembly 104 further has the first fracturing mechanism 116a and the second fracturing mechanism 116b. The first fracturing mechanism 116a has the first actuator arm 132a or first extending member 132a. The second fracturing mechanism has the second actuator arm 132b or second extending member 132b. The depending protrusions or projections 150a,150b depend from the extending members 132a,132b. In this exemplary embodiment, the first actuator arm 132a has a second hinge 194a defined by a second cut-out portion 196a in the first actuator arm 132a. The second hinge 194a assists the second segment 172a of the actuator arm in pivoting with respect to the first segment 170a of the actuator arm 132a,132b such as when using the depending rib or second segment 154a,154b of the depending protrusion to further manipulate the outer wall 50 of the plastic ampoule assembly 10 to force flowable material M from the dispenser 10. It is understood that the second actuator arm 132b could be considered to have a third hinge and fourth hinge when considered that the first actuator arm 132*a* can be considered to have a first hinge and a second hinge. It is understood that the descriptions regarding the first actuator arm 132*a* apply equally to the descriptions to the second actuator arm 132*b*. It is also understood that the actuator arms 132*a*,132*b* have a first neutral position when mounted on the plastic ampoule assembly 10 such as shown in FIG. 12. Applying a force F to the actuator arms 132*a*,132*b* pivot the arms 132*a*,132*b* about the base member 102 to an actuating position to fracture the membrane 52 of the plastic ampoule assembly 10.

Figure 13:
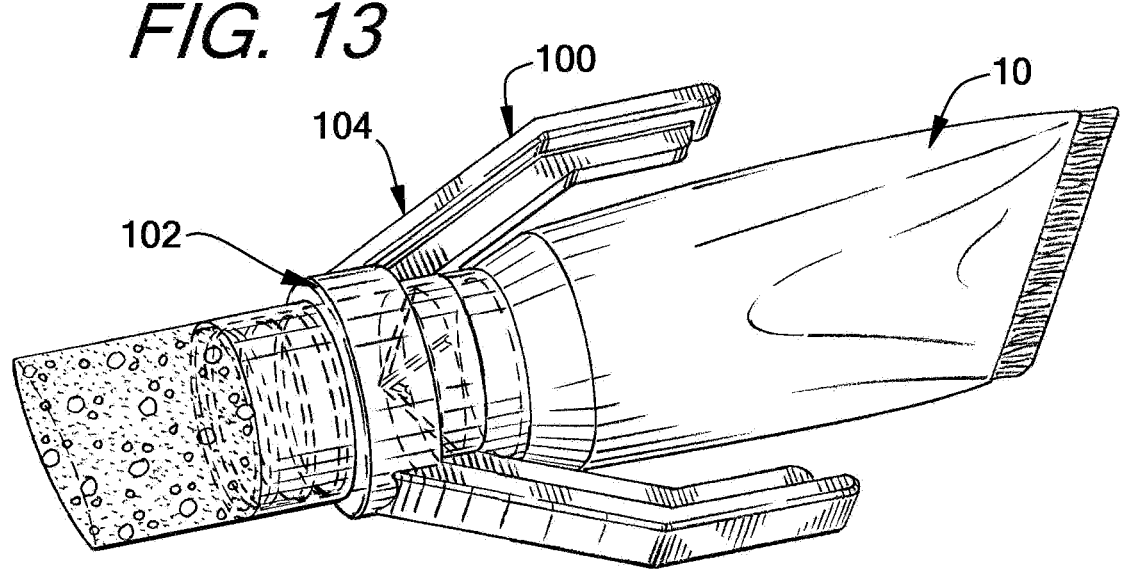
FIG. 13 is a perspective view of a dispenser actuator assembly according to another exemplary embodiment of the present invention, the dispenser actuator assembly mounted on a plastic ampoule assembly.
Figure 14:
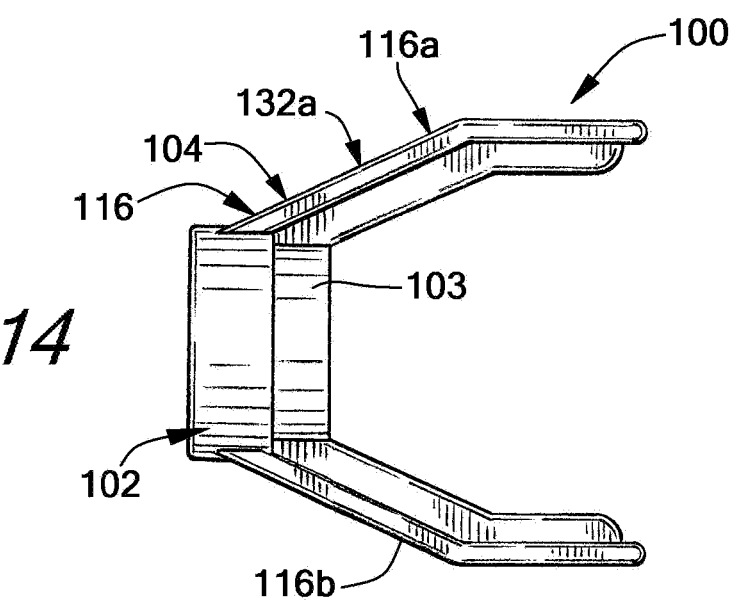
FIG. 14 is a side elevation view of the dispenser actuator assembly of FIG. 13.
Figure 15:
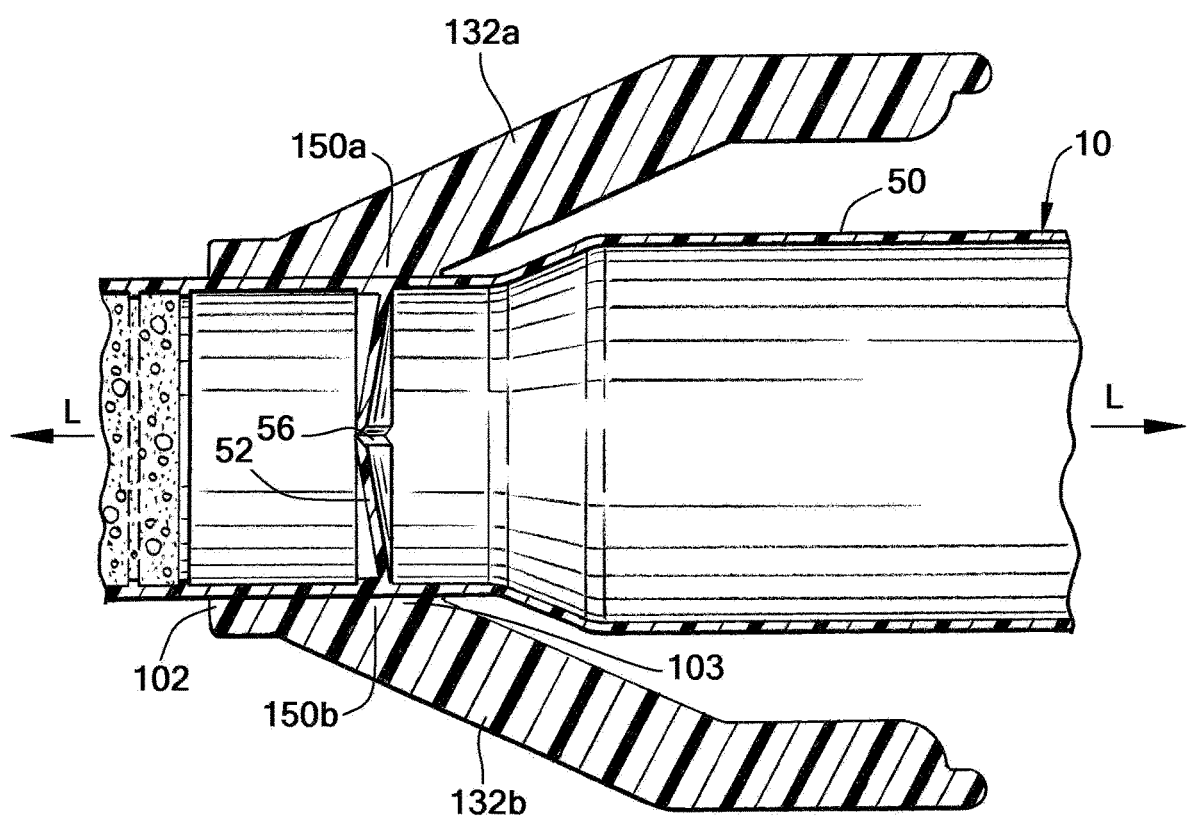
FIG. 15 is a partial cross-sectional view of the dispenser actuator assembly mounted on the plastic ampoule assembly shown in FIG. 9.

FIGS. 13-15 disclose another exemplary embodiment of the dispenser actuator assembly 100 of the present invention. Similar to the embodiments above, the dispenser actuator assembly 100 generally includes a base member 102 and an actuator assembly 104. This embodiment is similar to the embodiments described above wherein the actuator arms 132*a*,132*b* extend from the base member 102 and have multiple segments. In this embodiment, the depending protrusion 150 or projection is positioned on an underside of the actuator arm 132*a*,132*b* and is integral with an extended portion 103 of the base member 102. Thus, there is no gap or space between the projection 150*a* and the base member 102. As further shown in FIGS. 13-15, the depending protrusion or projection 150*a* has a first end connected to the first actuator arm 132*a* or first extending member 132*a* and a second end connected to the base member 102. The extending member 132*a* covers the projection 150*a*. As further shown, the projection 150 has a length that extends beyond the membrane 52 when mounted on the plastic ampoule assembly 10. Thus, the projection extends past a front side of the membrane 52 and a rear side of the membrane 52. When the base member 102 is positioned on the plastic ampoule assembly 10, the protrusion is positioned proximate the membrane 52. It is understood that the actuator arms 132*a*,132*b* supply a force F to the outer wall 50 to fracture the weld seam 56 of the membrane 52. It is understood that the descriptions regarding the first actuator arm 132*a* apply equally to the descriptions to the second actuator arm 132*b*. It is also understood that the actuator arms 132*a*,132*b* have a first neutral position when mounted on the plastic ampoule assembly 10 such as shown in FIG. 15. Applying a force F to the actuator arms 132*a*,132*b* pivot the arms 132*a*,132*b* about the base member 102 to an actuating position to fracture the membrane 52 of the plastic ampoule assembly 10.

Figure 19:
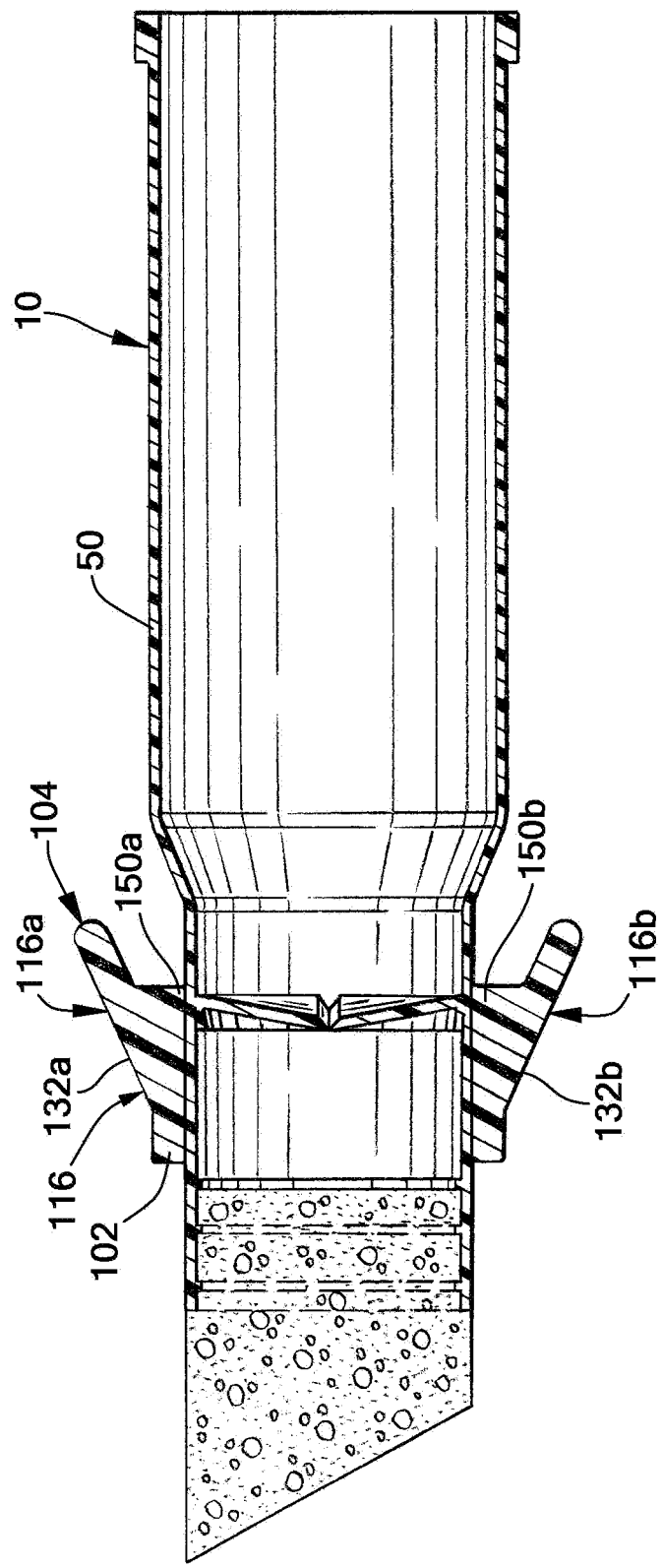
FIG. 19 is a cross-sectional view of the alternative embodiment of the dispenser actuator assembly mounted on the plastic ampoule assembly shown in FIG. 16.

FIGS. 16-19 disclose another exemplary embodiment of the dispenser actuator assembly 100 of the present invention. Similar to the embodiments above, the dispenser actuator assembly 100 generally includes a base member 102 and an actuator assembly 104. In particular, the structure is similar to the embodiment of FIGS. 13-15 wherein the projection 150 is integral with a portion of the base member 102. The actuator arm 132 is a singular arm and has a shorter dimension. The actuator arm 132 is dimensioned to receive a thumb pad of a user. The actuator arm 132 has an extending member that extends from the base member 102 and has a contoured surface. As further shown in FIGS. 16-18, an outer surface of the extending member of the actuator arm 132 is concave. FIG. 19 shows a further alternative exemplary embodiment having a first actuator arm 132*a* and a second actuator arm 132*b*. The first fracturing mechanism 116*a* and the second fracturing mechanism 116*b* are positioned on the base member 102 in opposed relation. In an exemplary embodiment, the mechanisms 116*a*,116*b* are generally 180 degrees apart. In this embodiment, there is no space or gap between the projection 150 and the container 48 when mounted on the plastic ampoule assembly 10. As shown in FIG. 15, the plastic ampoule assembly 10 defines a longitudinal axis. The extending member 132*a* has a first segment and a second segment connected to the first segment. The first segment extends from the base member or outer wall at an angle. The second segment extends from the first segment along an axis that is generally parallel to the longitudinal axis L as can be appreciated from FIG. 15. It is understood that the descriptions regarding the first actuator arm 132*a* apply equally to the descriptions to the second actuator arm 132*b*. It is also understood that the actuator arms 132*a*,132*b* have a first neutral position when mounted on the plastic ampoule assembly 10 such as shown in FIG. 18. Applying a force F to the actuator arms 132*a*,132*b* deflect the arms 132*a*,132*b* about the base member 102 to an actuating position to fracture the membrane 52 of the plastic ampoule assembly 10.

Figure 20:
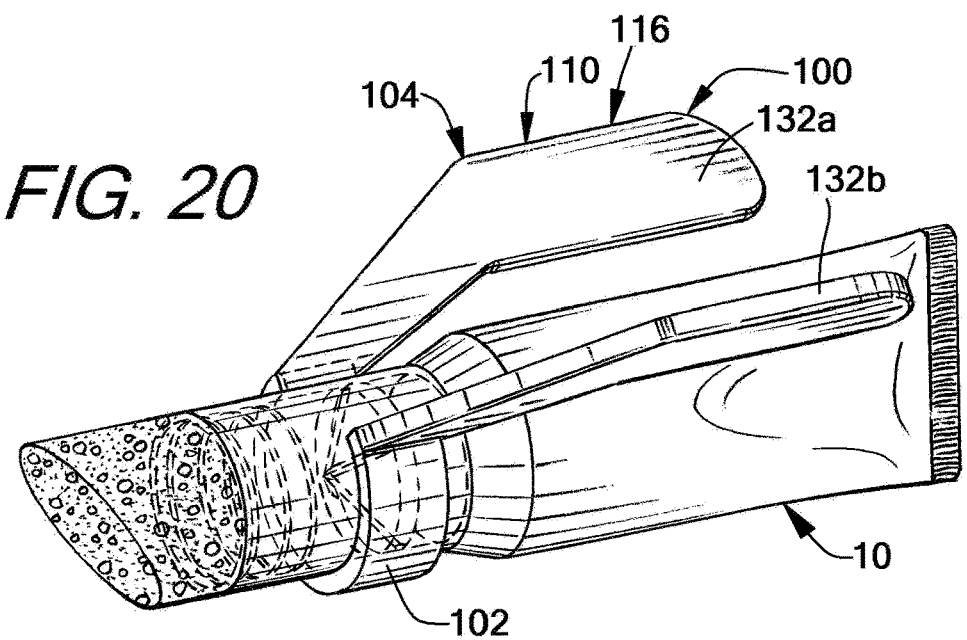
FIG. 20 is a perspective view of a dispenser actuator assembly according to an exemplary embodiment of the present invention, the dispenser actuator assembly mounted on a plastic ampoule assembly.
Figure 21:
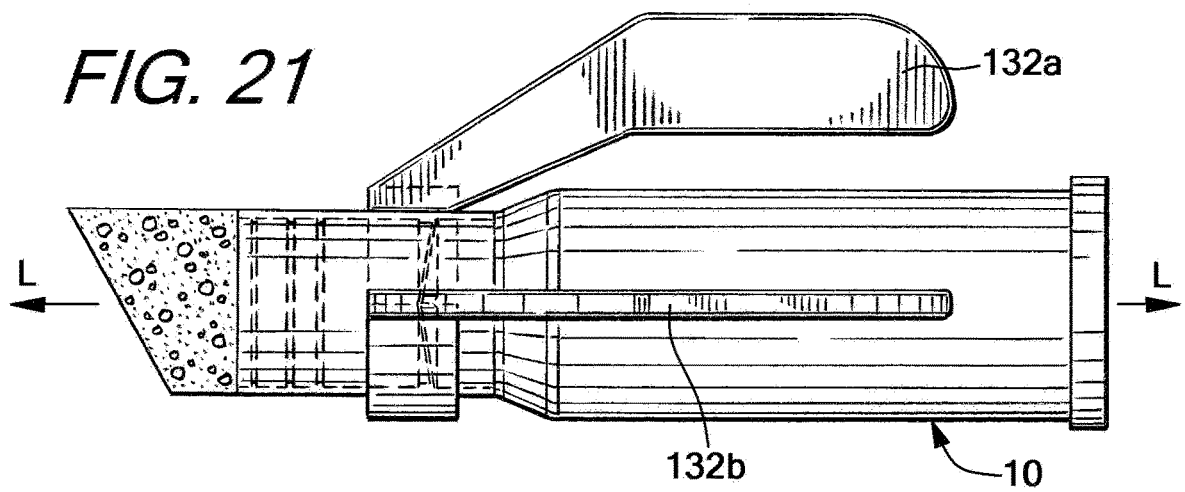
FIG. 21 is a top perspective view of the dispenser actuator assembly mounted on the plastic ampoule assembly shown in FIG. 20.
Figure 22:
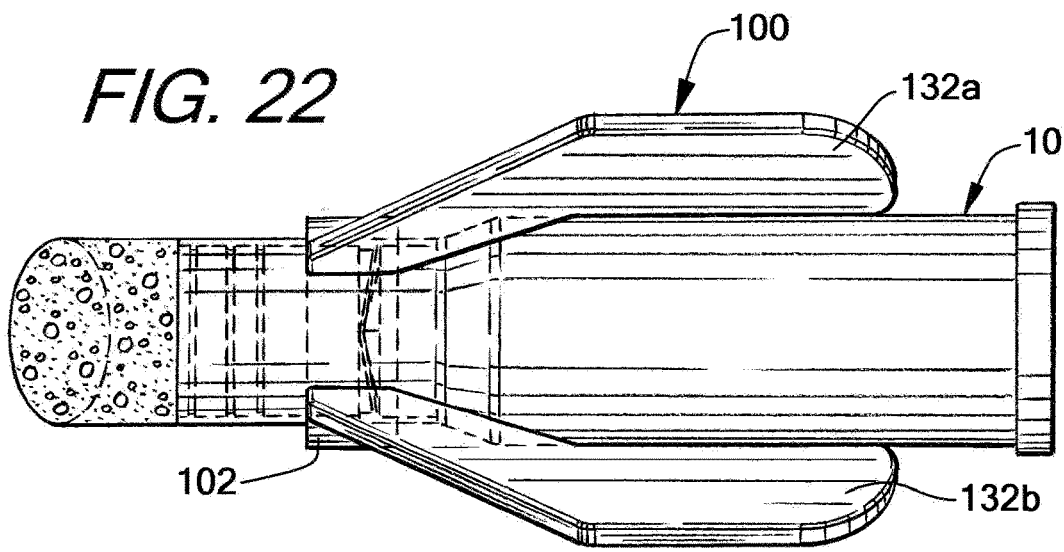
FIG. 22 is a top plan view of the dispenser actuator assembly mounted on the plastic ampoule assembly shown in FIG. 20.
Figure 23:
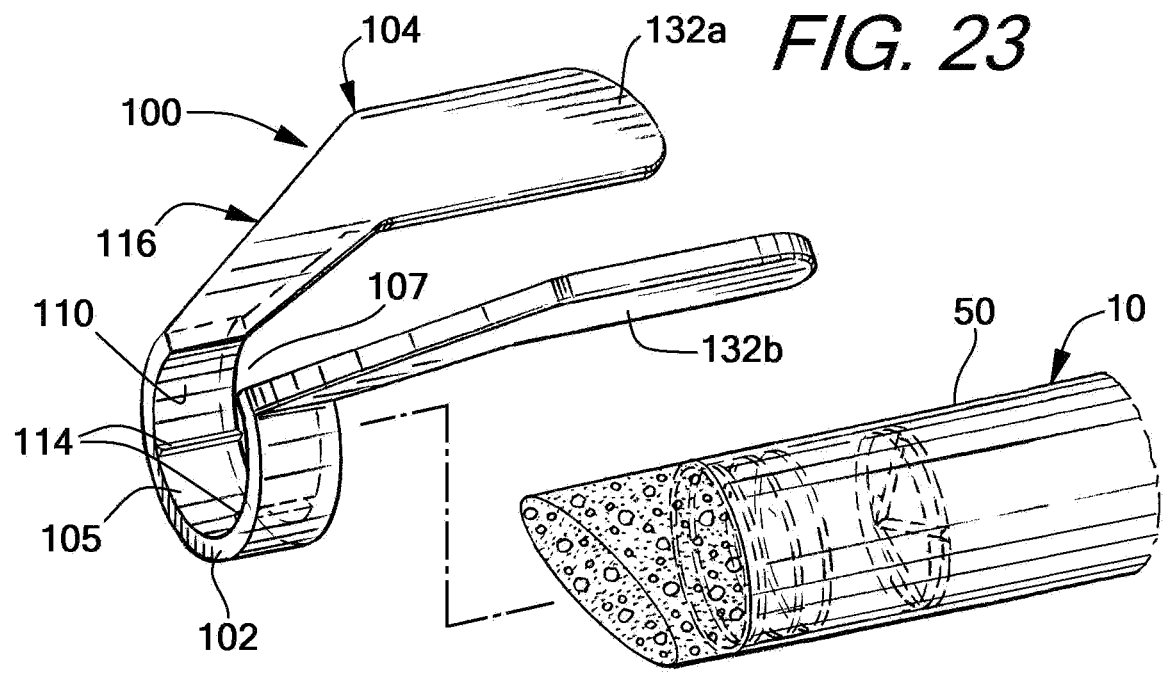
FIG. 23 is an exploded view of the dispenser actuator assembly and plastic ampoule assembly of the FIG. 20.
Figure 24:
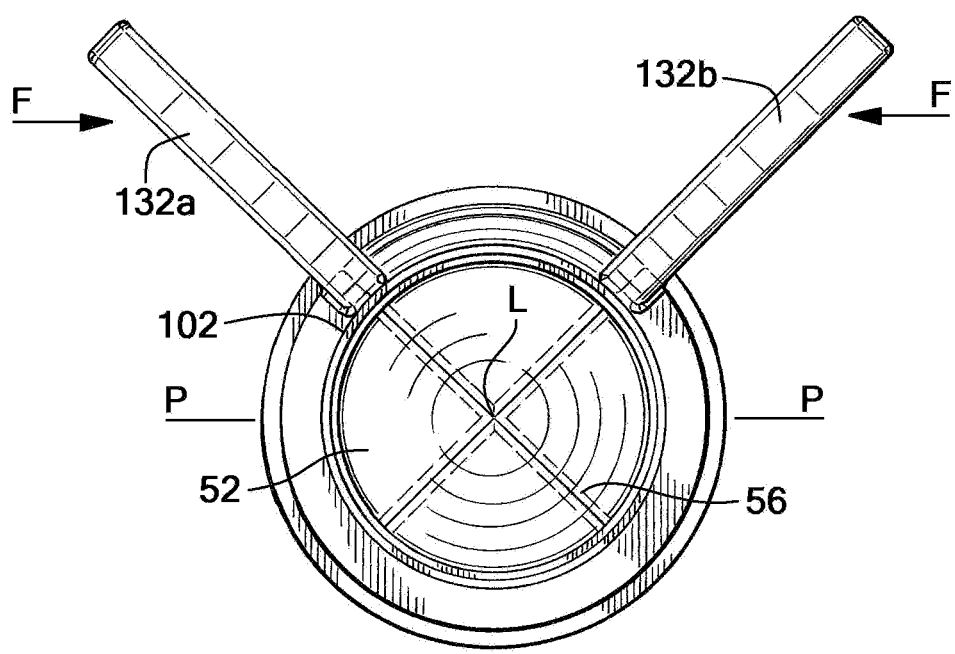
FIG. 24 is an end elevation view of the dispenser actuator assembly mounted on the plastic ampoule assembly of FIG. 20.
Figure 25:
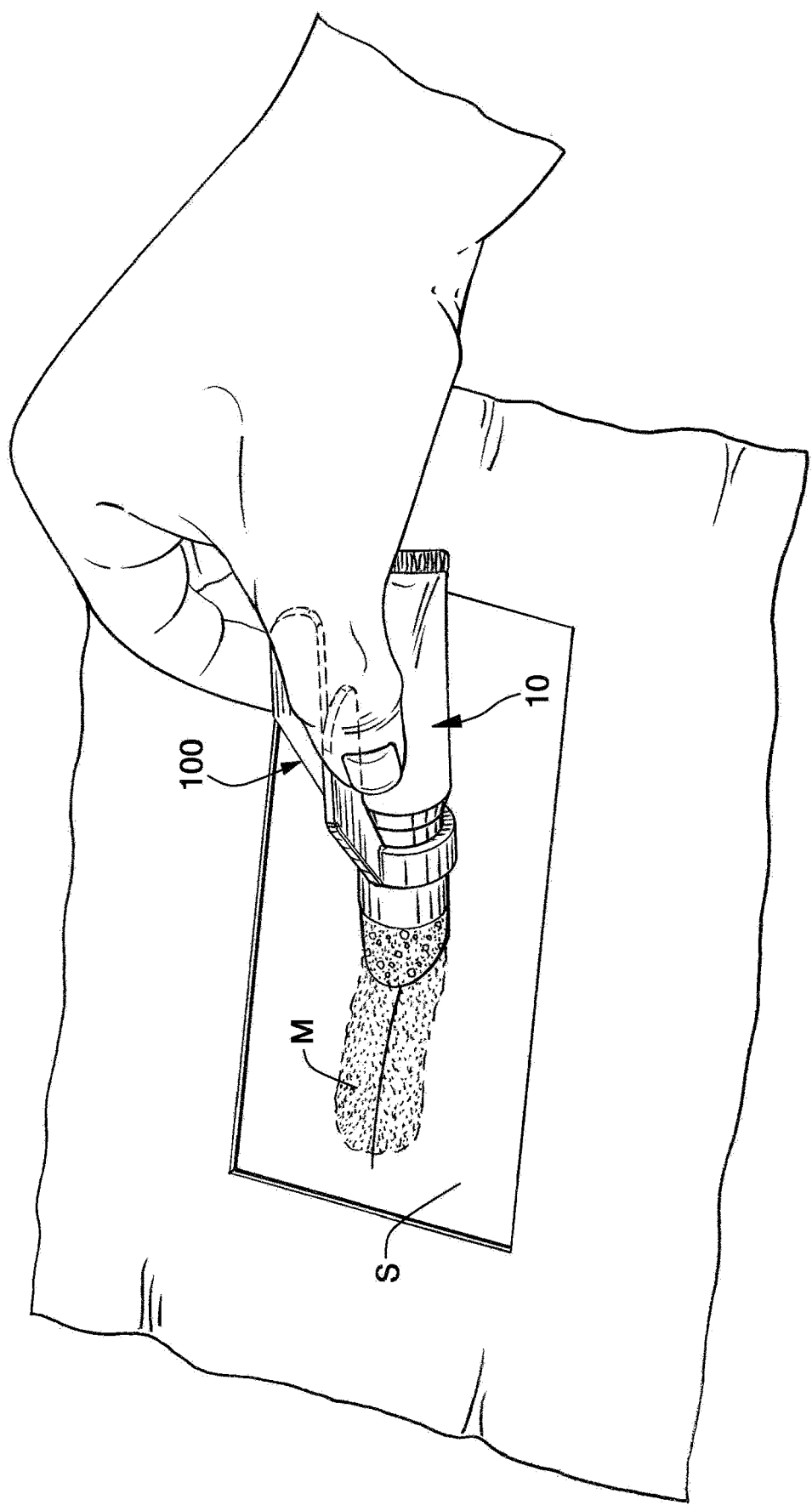
FIG. 25 is a perspective view of a user dispensing flowable material onto a receiving surface.

FIGS. 20-25 disclose another exemplary embodiment of the dispenser actuator assembly 100 of the present invention. Similar to the embodiments above, the dispenser actuator assembly 100 generally includes a base member 102 and an actuator assembly 104. In this embodiment, the base member 102 is not a full annular ring structure, but has break proximate one end or upper end of the base member 102. The base member 102 defines a collar 105 that is positioned around and on the outer wall 50 of the container 48. The collar 105 has a passageway 107 that is in communication with the opening 110 defined by the base member 102. The base member 102 has an arcuate shape and is dimensioned to fit generally around the outer wall of the plastic ampoule assembly 10. Thus, the base member 102 and collar 105 is connected to the plastic ampoule assembly 10 along a cylindrical contour of the outer wall 50 of the container 48. The base member 102 may also have the longitudinal ribs 114 as described above. As described above, the actuator assembly 104 is considered to have a fracturing mechanism 116 that has a first actuator arm 132*a* or first extending member 132*a* and a second actuator arm 132*b* or second extending member 132*b*. The actuator assembly 104 has a first actuator arm 132*a*, or first extending member 132*a* and a second actuator arm 132*b*, or second extending member 132*b*. The actuator arms 132*a*,132*b* extend away from the base member 132 at an angle. In particular, the actuator arms 132*a*,132*b* extend from the collar 105. The arms have a first segment and a second segment. The first segment extends from the base member 102 at an angle. The second segments, when the assembly 100 is mounted on the plastic ampoule assembly 10, extend generally parallel to a longitudinal axis of the plastic ampoule assembly 10. The actuator arms 132*a*,132*b* are positioned on the container 48 in a radially spaced relation and also generally spaced above the longitudinal axis L. Stated differently, the arms 132*a*,132*b* are positioned above a plane P that passes through the longitudinal axis L of the dispenser 10. Thus, the actuator arms 132*a*,132*b*, or extending members 132*a*,132*b* are remote from the plane defined through the longitudinal axis L of the plastic ampoule assembly 10. The arms 132*a*,132*b* have a neutral position such as shown in FIG. 22. To actuate, a user presses the actuator arms towards one another. As can be appreciated from FIG. 24, the base member 102, which is positioned generally around the outer wall 50 at the membrane 52, is moved inwardly to apply a force F to the membrane 52. Upon application of the force F, the weld seam 56 fractures wherein flowable material can be dispensed from the dispenser 10 onto a receiving surface S as shown in FIG. 25. It is understood that the descriptions regarding the first actuator arm 132*a* apply equally to the descriptions to the second actuator arm 132*b*. It is also understood that the actuator arms 132*a*,132*b* have a first neutral position when mounted on the plastic ampoule assembly 10 such as shown in FIG. 20. Applying a force F to the actuator arms 132*a*,132*b* moves the arms 132*a*,132*b* towards one another to an actuating position to fracture the membrane 52 of the plastic ampoule assembly 10 as can be appreciated from FIG. 24.

FIGS. 26-30 disclose another exemplary embodiment of the dispenser actuator assembly 100 of the present invention. Similar to the embodiments above, the dispenser actuator assembly 100 generally includes a base member 102 and an actuator assembly 104. The structures of FIGS. 26-30 are similar to the structures of FIGS. 20-25, which description applies to FIGS. 26-30.

Figure 26:
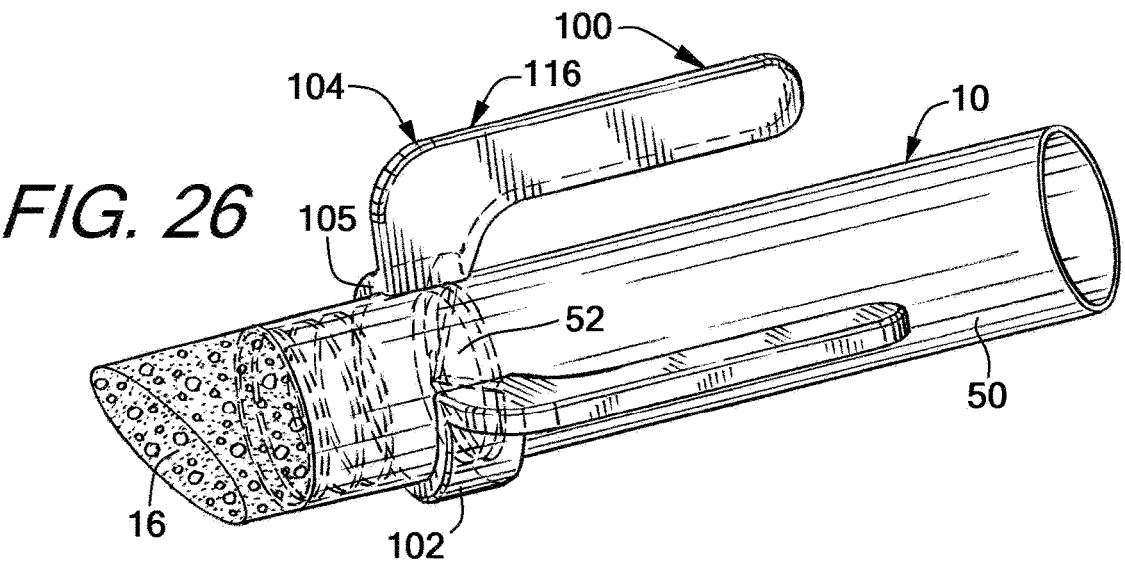
FIG. 26 is a perspective view of a dispenser actuator assembly according to another exemplary embodiment of the present invention, the dispenser actuator assembly mounted on a plastic ampoule assembly.
Figure 27:
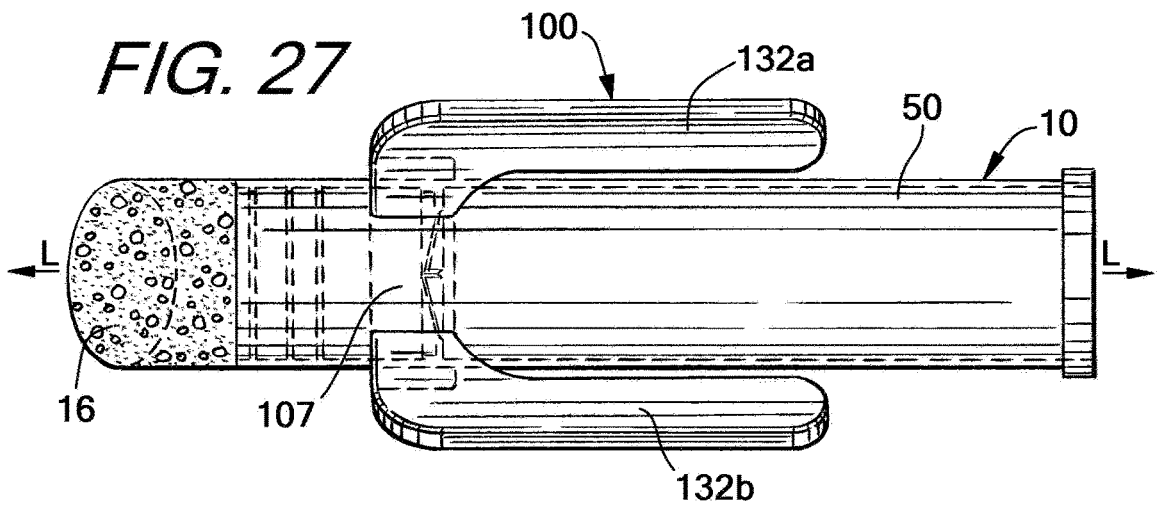
FIG. 27 is a top plan view of the dispenser actuator assembly mounted on the plastic ampoule assembly shown in FIG. 26.
Figure 28:
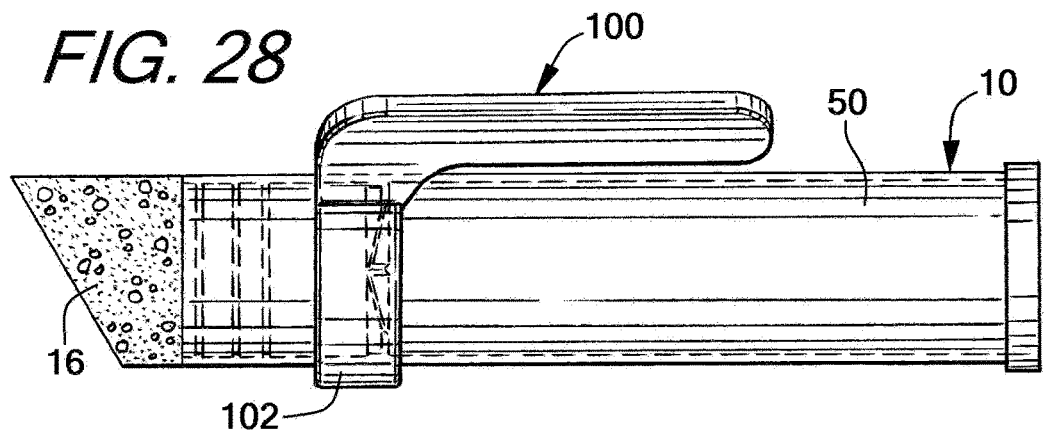
FIG. 28 is a side elevation view of the dispenser actuator assembly mounted on the plastic ampoule assembly shown in FIG. 26.
Figure 29:
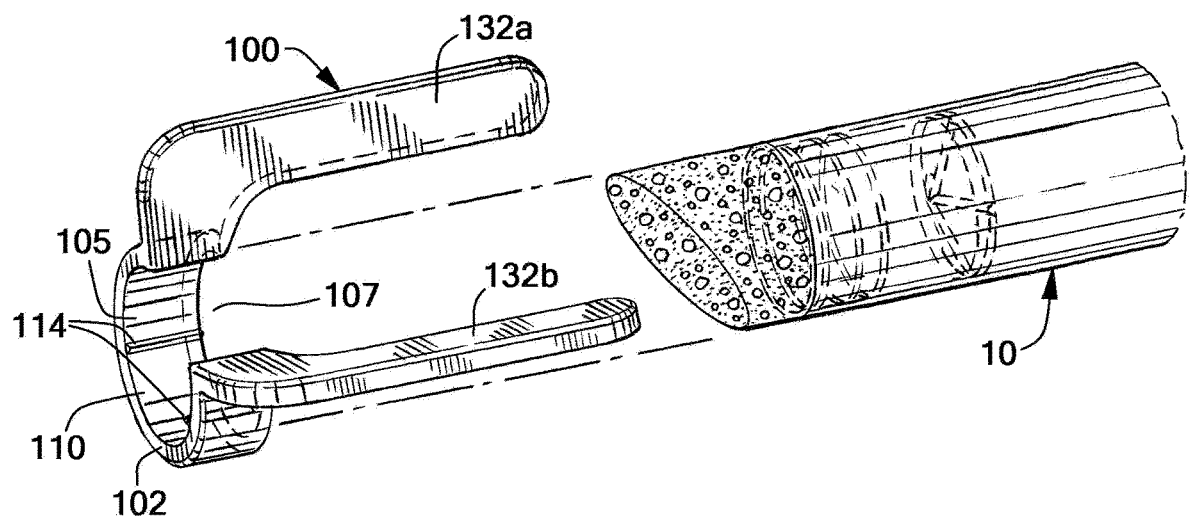
FIG. 29 is an exploded view of the dispenser actuator assembly and plastic ampoule assembly of the FIG. 26.
Figure 30:
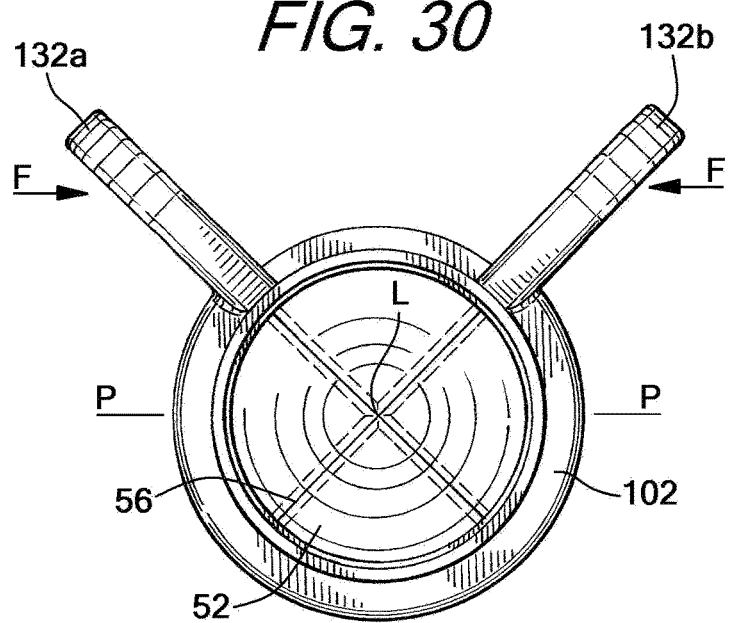
FIG. 30 is an end elevation view of the dispenser actuator assembly mounted on the plastic ampoule assembly of FIG. 26.

As described above, the dispenser actuator assembly 100 of FIGS. 26-30 generally includes a base member 102 and an actuator assembly 104. In this embodiment, the base member 102 is not a full annular ring structure, but has break proximate one end or upper end of the base member 102. The base member 102 defines a collar 105 that is positioned around and on the outer wall 50 of the container 48. The collar 105 has a passageway 107 (FIGS. 27 and 29) that is in communication with the opening 110 defined by the base member 102. The base member 102 has an arcuate shape and is dimensioned to fit generally around the outer wall of the plastic ampoule assembly 10. Thus, the base member 102 and collar 105 is connected to the plastic ampoule assembly 10 along a cylindrical contour of the outer wall 50 of the container 48. The base member may also have the longitudinal ribs 114 as described above. As described above, the actuator assembly 104 is considered to have a fracturing mechanism 116 that has a first actuator arm 132*a* or first extending member 132*a* and a second actuator arm 132*b* or second extending member 132*b*. The actuator assembly 104 has a first actuator arm 132*a*, or first extending member 132*a* and a second actuator arm 132*b*, or second extending member 132*b*. The actuator arms 132*a*,132*b* extend away from the base member 132. In particular, the actuator arms 132*a*,132*b* extend from the collar 105. The arms have a first segment and a second segment. The first segment extends from the base member 102 generally normal to a longitudinal axis L of the plastic ampoule assembly 10. The first segments further extend upwards from the collar 105. The second segments, when the assembly 100 is mounted on the plastic ampoule assembly 10, extend generally parallel to the longitudinal axis L of the plastic ampoule assembly 10. The actuator arms 132*a*,132*b* are positioned on the container 48 in a radially spaced relation and also generally spaced above the longitudinal axis L. Stated differently, the arms 132*a*,132*b* are positioned above a plane P that passes through the longitudinal axis L of the dispenser 10. Thus, the actuator arms 132*a*,132*b*, or extending members 132*a*,132*b* are remote from the plane defined through the longitudinal axis L of the plastic ampoule assembly 10 (FIG. 30). The arms 132*a*,132*b* have a neutral position such as shown in FIG. 26. To actuate, a user presses the actuator arms towards one another. As can be appreciated from FIG. 30, the base member 102, which is positioned generally around the outer wall 50 at the membrane 52, is moved inwardly to apply a force F to the membrane 52. Upon application of the force F, the weld seam 56 fractures wherein flowable material can be dispensed from the dispenser 10 onto a receiving surface S similar to as shown in FIG. 25 with the previous embodiment. It is understood that the descriptions regarding the first actuator arm 132*a* apply equally to the descriptions to the second actuator arm 132*b*. It is also understood that the actuator arms 132*a*,132*b* have a first neutral position when mounted on the plastic ampoule assembly 10 such as shown in FIG. 26. Applying a force F to the actuator arms 132*a*, 132*b* moves the arms 132*a*,132*b* towards one another to an actuating position to fracture the membrane 52 of the plastic ampoule assembly 10 as can be appreciated from FIG. 30.

As discussed, in an exemplary embodiment, the dispenser actuator assembly 100 is formed as a single unit in an injection molding process. Mold members are structured to provide a mold cavity in the form of the dispenser actuator assembly 100.

It is understood that additional features can be incorporated into the molding process. The gates for injecting molding material into the mold can be varied to achieve desired characteristics in the assembly. In a further exemplary embodiment, a multi-shot molding process could be utilized. For example, a two-shot molding process could be utilized wherein certain portions of the assembly 100 are molded from a more flexible material while other structures of the assembly 100 are formed from a more rigid material.

The dispenser actuator assembly 100 can be formed in the injection molding process from a variety of different injected molded materials. Selection of the material will depend on the desired operational characteristics of the assembly 100 such as the amount of rupturing force to be generated. The assembly 100 could be formed from polyolefin family of resins. The material could be polyethylene or polypropylene and a combination thereof. The material could also be nylon. Because of the structural features described above, it is possible to use more rigid/brittle materials as well as materials having a higher flexural modulus. The material could also be amorphous polymers including acrylic, acrylonitrile butadiene styrene, or polycarbonate. The material for the assembly 100 could further be a polyvinylidene fluoride (PVDF) material. With the broader selection of materials possible, the assembly 100 can also be used in a broader range of applications requiring rupturing of different types of containers. The dispenser actuator assembly 100 could also be made of materials for specialty application such as materials that are capable of being autoclavable.

It is understood that the dispenser actuator assembly 100 and the glass ampoule assembly 10/plastic ampoule assembly 10 may be distributed or sold as a kit, e.g., together as a single unit package. The dispenser actuator assembly 100 may be mounted on the glass ampoule assembly 10 generally proximate a central intermediate segment of the glass ampoule assembly 10 to form a tandem unit. The tandem unit can be placed in a package assembly such as a blister package having a recess to receive the tandem unit. A cover member can be used to enclose the tandem unit. The kit could include the dispenser actuator assembly 100 packaged with a dispenser 10. The dispenser 10 could be the traditional glass ampoule assembly 10 or a plastic ampoule assembly 10, or both if desired.

Prior to the invention, a user typically must squeeze, via finger pressure, the outer container 14 of the glass ampoule assembly 10 to rupture the glass ampoule 12. The squeezing thumb/fingers provides a force to deform the outer container 14 and rupture the glass ampoule 12. The required finger pressure could be considered significant for certain users having limited strength in their respective digits. The dispenser actuator assembly 100 provides mechanical advantage from the actuator arms 132*a*,132*b* wherein the required finger pressure can be reduced. Thus, in some exemplary embodiments, the glass ampoule assembly 10 can take approximately 15-20 psi when finger pressure is applied to the assembly 10. With the dispenser actuator assembly 10, the pressure/force can be reduced to approximately 3-4 psi. Similar results can be achieved with a plastic ampoule assembly 10. A significant reduction in required psi is achieved with the dispenser actuator assembly 100. It is understood that the dispenser actuator assembly 100 could include alternative features to provide further reduction is required psi as desired. It is understood that the angle that the actuator arms 132a,132b extend from the base member 102 can vary and set at a greater angle that would allow more force to be generated. This can lead to a more difficult grip for certain users and, therefore, a sufficient angle is determined to provide the necessary rupturing force with an ergonomically-friendly grip of a user.

The dispenser actuator assembly 100 provides several benefits. The actuator assembly provides mechanical advantage for a user to rupture or fracture the dispenser. The actuator arms can vary in length and resiliency to provide a desired mechanical force in rupturing the dispenser. Because the dispenser actuator assembly allows for a user to apply an increased force than from finger pressure alone, the assembly can be used to rupture more robustly designed dispensers. Such dispensers may be designed to rupture under an increased force to minimize the chances of inadvertent rupture. In addition, the dispenser actuator assembly is designed to rupture the glass ampoule at the optimal location at the interface area proximate the domed-portion of the glass ampoule to enhance the rupturing of the glass ampoule. The dispenser actuator assembly can also be positioned proximate a membrane of a plastic ampoule assembly. Furthermore, as the user engages the actuator arms of the assembly rather than directly engaging the outer container of the dispenser, the chances that glass shards from the ruptured glass ampoule can injure the fingers or hand of the user is minimized. The dispenser actuator assembly can also be adjustably mounted along a length of the glass ampoule assembly. For example, the dispenser actuator assembly can be slid along a length of the outer container of the glass ampoule assembly to a desired location. This helps in further manipulating flowable material from the glass ampoule assembly. In addition, the dispenser actuator assembly 100 can be removable attached to the dispenser. Once the dispenser is ruptured and the flowable material is dispensed from the dispenser, the dispenser actuator assembly can be removed from the dispenser and used to rupture multiple other dispensers. It is understood as well that the dispenser actuator assembly 100 could be manufactured as a single-use assembly that is discarded. It is further understood that the assembly 100 can be positionally adjusted on the glass ampoule assembly 10 to manipulate flowable material as desired or break the glass ampoule at a particular location.

The dispenser 10 is permitted to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

The dispenser used with the dispenser actuator assembly of the present invention is designed to primarily contain and dispense flowable materials that are fluids. Other flowable materials can also be dispensed. For example, the flowable material could be a liquid, powder, gel or other type of flowable substance or flowable material. Also, in other embodiments such as dispensers containing multiple chambers for different flowable materials, the flowable materials M1, M2 could both be fluids. In another embodiment, the first flowable material M1 could be a liquid, and the second flowable material M2 could be a powder to be mixed with the fluid. Other combinations depending on the use are also permissible.

This permits the dispenser 10 to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

In one example, the dispenser of the present invention can be used in medical applications. In one particular exemplary embodiment, the dispenser may contain a surgical antiseptic such as for cleaning and preparing a body area for incision, and sometimes referred to as a surgical prep solution. One type of antiseptic may be chlorohexidine gluconate (CHG). This CHG-based antiseptic could also be combined with a medical sealant such as cyano-acrylic wherein the dispenser is used to contain and dispense cyano-acrylic chlorohexidine gluconate (CACHG). Other types of medical sealants could also be used. Other types of antiseptics could be iodine-based such as iodophoric skin tinctures, which are commercially available. Other antiseptics and antimicrobial agents could also include other iodine-based complexes, alcohol-based complexes or peroxides. Additional additives may also be used with the antiseptic such as colorants. A single chamber dispenser may be used in such an application, but a multi-chamber dispenser such as disclosed herein may also be used.

In another example, the dispenser of the present invention can be used in adhesive-type applications. The dispenser can dispense a flowable material or mixture that is an adhesive, epoxy, or sealant, such as an epoxy adhesive, craft glue, non-medical super glue and medical super glue. The dispenser could also be used with shoe glue, ceramic epoxy and formica repair glue. The dispenser could further be used for a variety of other adhesive dispensing applications, mastic-related resins or the like.

In another example, the dispenser of the present invention can be used in automotive applications. The dispenser can dispense a flowable material or mixture that is an automotive product, such as a rear view mirror repair kit, a vinyl repair kit, auto paints, an auto paint touch up kit, a window replacement kit, a scent or air freshener, a windshield wiper blade cleaner, a lock de-icer, a lock lubricant, a liquid car wax, a rubbing compound, a paint scratch remover, a glass/mirror scratch remover, oils, radiator stop-leak, a penetrating oil, or a tire repair patch adhesive. Other automotive applications could include acetone-based products such as windshield primer. Additional automotive applications could be for general auto/motorcycle or bicycle repair kits including chain oils.

In another example, the dispenser of the present invention can be used in chemistry-related applications. The dispenser can dispense a flowable material or mixture that is a chemistry material such as a laboratory chemical, a buffer solution, a rehydration solution of bacteria, a biological stain, or a rooting hormone. The dispenser may also be used as a chemical tester. In one such application, the dispenser can be used for testing drinks for various "date rape" drugs. Other types of chemical testers are also possible. The dispenser could be used to contain various types of chemicals including solvents. In a particular application, the additional material formulations used to form the dispenser allow the dispenser to store and dispense methyl ethyl ketone.

In another example, the dispenser of the present invention can be used to dispense a flowable material or mixture is a cosmetic and beauty supply/toiletry product. For example, the dispenser can be used for a nail polish, lip gloss, body cream, body gel, body paints, hand sanitizer, nail polish remover, liquid soaps, skin moisturizers, skin peels, tooth whiteners, hotel samples, mineral oils, toothpastes, mouthwash or sunscreens. The flowable material could also be a fragrance such as women's perfume or men's cologne. The flowable material could also be tattoo inks. The flowable material could be used for solutions for treating and/or removing tattoo ink.

The cosmetic applications could also include hair care type applications. In another particular example, the dispenser of the present invention can be used in a hair dye kit. Certain hair dye kits come in multiple components that are separately stored wherein the dispenser embodiment disclosed herein having a dividing wall that cooperates to define separate chambers can be utilized. Thus, the dispenser of the present invention can be used in a two-part hair care product such as a hair dye kit. A first flowable substance of the hair dye kit can be carried in the first chamber, and a second flowable substance of the hair dye kit can be carried in the second chamber. The membrane is ruptured wherein the two flowable substances can be mixed together to form a mixture or solution. The mixture or solution can then be dispensed from the dispenser onto the hair of a user. The dispenser can also dispense a flowable material or mixture in other hair care products, such as hair bleaches, hair streaking agent, hair highlighter, shampoos, other hair colorants, conditioners, hair gels, mousse, hair removers, or eyebrow dye.

In another example, the dispenser of the present invention can be used in crafting applications or stationary products. The dispenser can also dispense a large variety of stationery or craft products, such as magic markers, glitter gels, glitter markers, glitter glues, gel markers, craft clues, fabric dyes, fabric paints, permanent markers, dry erase markers, dry eraser cleaner, glue sticks, rubber cement, typographic correction fluids, ink dispensers and refills, paint pens, counterfeit bill detection pen, envelope squeeze moisturizers, adhesive label removers, highlighters, and ink jet printer refills.

In another example, the dispenser of the present invention can also dispense a flowable material or mixture that is an electronics-related product. For example, the electronics product could be a cleaning compound, a telephone receiver sanitizer, cell phone cleaner or protectants, a keyboard cleaner, a cassette recorder cleaner, audio/video disc cleaner, a mouse cleaner, or a liquid electrical tape.

In another example, the dispenser of the present invention can dispense a flowable material or mixture in food product applications. For example, the food product may be food additives, food colorings, coffee flavorings, cooling oils, spices, flavor extracts, food additives, drink additives, confections, cake gel, pastry gel, frostings, sprinkles, breath drops, condiments, sauces, liquors, alcohol mixes, energy drinks, or herbal teas and drinks.

In another example, the dispenser of the present invention can be used in home repair product and home improvement applications. The dispenser can also dispense a flowable material that is a home repair product, such as a caulking compounds or materials, a scratch touch up kit, a stain remover, a furniture repair product, a wood glue, a patch lock, screw anchor, wood tone putty or porcelain touch-up. The dispenser could also dispense a plumbing flux applicator, rust remover and tree wound treatment. In certain home repair or home improvement applications, the dispenser can be used in paint applications. The dispenser can dispense a variety of paint products such as general paints including interior/exterior paints, novelty paints, paint additives, wood stain samples, varnishes, stains, lacquers, caulk, paint mask fluid or paint remover.

In another example, the dispenser of the present invention can be used in household related products. For example, the dispenser could be used for cleaning agents, pest control products, a fish tank sealant or a fish tank treatment, a leak sealant, a nut/bolt locker, screw tightener/gap filler, a super glue remover or goo-b-gone. The dispenser could also be used for a colorant dispenser, or disinfectants, a plant food, fertilizers, bug repellants or a cat litter deodorant. The dispenser could also dispense toilet dyes and treatments, eyeglass cleaners, shoe polishes, clothing stain removers, carpet cleaners and spot removers, multi-purpose oils, and ultrasonic cleaner concentrate. The household product could include a variety of pet-related products including but not limited to an animal medicine dispenser, pet medications, animal measured food dispenser, pet shampoos or odor eliminator liquids. A large variety of pest control products can be dispensed by the dispenser, including insect attractants, pesticides, pet insect repellants, pest sterilizers, insect repellants, lady bug attractant and fly trap attractant. The household product could also include various types of polishes, reagents, indicators and other products.

In another example, the dispenser of the present invention can be used in lubricant applications. The dispenser can dispense a large variety of lubricants including industrial lubricants, oils, greases, graphite lubricants or a dielectric grease.

The dispenser of the present invention can also be used in other medical applications including medical related products, medicinal products and medicaments. Additional medical related product applications can include skin adhesive kits to be used in place of traditional stitching products. As discussed, the dispenser could also be used with topical antiseptics, antimicrobials and surgical scrub products. In addition, the dispenser 10 can dispense a large variety of medicinal products, such as blister medicines, cold sore treatments, insect sting and bite relief products, skin cleaning compounds, skin sealing solutions, skin rash lotions, nasal sanitizers, nasal medications, tissue markers, topical antimicrobials, topical demulcent, treatments for acne such as acne medications, umbilical area antiseptics, cough medicines, waterless hand sanitizers, toothache remedies, cold medicines, sublingual dosages or wart treatments. For example, the dispenser could contain a medicinal product containing hydrogen-peroxide used for dermatological conditions such as warts, seborrheic keratosis or similar skin conditions. The dispenser could also be used to dispense compositions for treating various other skin conditions. The dispenser could also be used in conjunction with a medical device product. Other medical related applications could include various types of dental related products including different types of compounds and treatments applied to a patients' teeth. The dispenser could also be used in veterinary related products.

In another example, the dispenser of the present invention can be used in novelty products. For example, the dispenser can contain materials in a glow-stick device. In such instance, the dispenser is a container that may contain multiple components separately stored until activation to create a glowing state in response to mixture of the components. Furthermore, the dispenser can dispense a flowable material or mixture that is a chemiluminescent light, a Christmas tree scent, a glitter gel, and a face paint. Other types of novelty paints could also be used with the dispenser.

In another example, the dispenser of the present invention can be used in sports products. The dispenser can dispense a variety of sports products including sports eye black, football hand glue, and baseball glove conditioner and pine tar. The dispenser can also dispense wildlife lures. The dispenser can be used in various camping related applications including portable lighting fuels for camp lights or other devices and tent repair kits. The dispenser can also be used in bingo or other game markers.

In another example, the dispenser of the present invention can be used in test kit applications. The dispenser can dispense a flowable material or mixture that is a test kit, such as a lead test kit, a drug kit, a radon test kit, a narcotic test kit, a swimming pool test kit (e.g., chlorine, pH, alkalinity etc.), a home water quality tester, a soil test kit, a gas leak detection fluid, a pregnancy tester, or a respirator test kit. The dispenser can also dispense a flowable material or mixture that as part of a medical device test kit, such as a culture media, a drug monitoring system, a microbiological reagent, a *streptococcus* test kit, or a residual disinfectant tester. The dispenser may also be used in diagnostic testing kits, explosive testing kits or other test kits. The dispenser can be used in breathalyzer tests, culture media samples and drug test kits.

In another example, the dispenser of the present invention can be used in personal care products or wellness-related products. The dispenser can also dispense a flowable material or mixture that is a personal care product, such as shaving cream or gel, aftershave lotion, skin conditioner, skin cream, skin moisturizer, petroleum jelly, insect repellant, personal lubricant, ear drops, eye drops, nose drops, corn medications, nail fungal medication, aging liquids, acne cream, contact lens cleaner, denture repair kit, finger nail repair kit, liquid soaps, sun screen, lip balm, tanning cream, self-tanning solutions, eye wash solution finger nail repair kits. The dispenser can also be used with aroma therapy products and homeopathic preparations. The dispenser can also dispense various vitamins, minerals, supplements and pet vitamins.

The dispenser can also dispense a flowable material or mixture in a variety of other miscellaneous applications. Such miscellaneous applications may include, but not be limited to use in connection with a suction device for culture sampling, taking various liquid samples or taking various swabbing samples. The dispenser could also be used for float and sinker devices, dye markers, microbiological reagents, and also for manufacturing parts assembly liquids and irrigation solutions. The dispenser may also be used as a chalk dispenser such as in construction applications.

Thus, the dispenser can be used in many different applications including mechanical, chemical, electrical or biomedical uses. The dispenser can dispense any variety of flowable materials including liquids and powders, and further including a liquid and a powder, two or more powders, or two or more liquids. The dispenser may be used as part of 2-part system (mix before use) including a liquid with a powder, a liquid with a liquid, a powder with a powder, or sealed inside another tube or product container or partially sealed, connected or attached to another container. The dispenser may also be used as part of a plunger dispensing system.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. A dispenser actuator assembly for actuating a dispenser for dispensing a flowable material, the dispenser in the form of a plastic ampoule assembly having a container having an outer wall and membrane collectively defining a first chamber containing the flowable material, the membrane having a thickness and a weld seam, the weld seam having a thickness less than the thickness of the membrane, the dispenser actuator assembly comprising:
   a base member having an opening configured to mount on the container; and
   a fracturing mechanism operably connected to the base member, the fracturing mechanism having a first extending member and a second extending member, the first extending member and the second extending member positioned on the base member in opposed relation to define a first neutral position, each extending member having a projection positioned proximate the membrane when the base member is configured to be mounted on the container, wherein in response to deflection of the extending members towards one another to an actuating position, the projections are configured to deflect the outer wall proximate the membrane wherein the weld seam is configured to fracture to create an opening through the membrane configured to allow the flowable material to pass therethrough and from the container.

2. The dispenser actuator assembly of claim 1 wherein the base member is an annular ring dimensioned to be configured to fit circumjacently around the outer container in an interference fit.

3. The dispenser actuator assembly of claim 2 wherein the annular ring defines an inner surface, the inner surface having a plurality of ribs extending from the inner surface, the ribs configured to engage the outer container when the base member is mounted on the container.

4. The dispenser actuator assembly of claim 1 wherein the opening of the base member extends completely through the base member.

5. The dispenser actuator assembly of claim 1 wherein the projections are configured to be spaced from the outer wall of the container prior to deflection of the extending members.

6. The dispenser actuator assembly of claim 1 wherein the projections depend from an underside of the extending members.

7. The dispenser actuator assembly of claim 1 wherein the projections have a length configured to extend beyond the membrane when the base member is mounted on the container.

8. The dispenser actuator assembly of claim 1 wherein the projections have a contoured surface, the contoured surface configured to deflect the outer wall in response to the deflection of the extending members.

9. The dispenser actuator assembly of claim 1 wherein the first extending member has a cut-out portion proximate an end of the first extending member extending from the base member, the cut-out portion defining a first hinge of the first extending member wherein the first extending member deflects about the first hinge, and the second extending member has a cut-out portion proximate an end of the second extending member extending from the base member, the cut-out portion defining a first hinge of the second extending member wherein the second extending member deflects about the first hinge.

10. The dispenser actuator assembly of claim 1 wherein the extending members have a first segment and a second segment, the respective first segments projecting from the base member.

11. The dispenser actuator assembly of claim 10 wherein the second segment has a rib depending therefrom, the depending rib configured to further deflect the outer wall of the container to force the flowable material through the membrane.

12. The dispenser actuator assembly of claim 10 wherein an interface area is defined between the first segment and the second segment wherein the interface area has a second cut-out portion defining a second hinge wherein the second segment is configured to pivot about the second hinge towards the outer wall.

13. The dispenser actuator assembly of claim 12 wherein the second cut-out portion is positioned on an exterior surface of the extending member.

14. A dispenser actuator assembly for actuating a dispenser for dispensing a flowable material, the dispenser in the form of a plastic ampoule assembly having a container having an outer wall and membrane collectively defining a first chamber containing the flowable material, the membrane having a thickness and a weld seam, the weld seam having a thickness less than the thickness of the membrane, the dispenser actuator assembly comprising:
a base member having an opening configured to mount on the container; and
a fracturing mechanism operably connected to the base member, the fracturing mechanism comprising:
a first extending member projecting from the base member, the first extending member having a first segment and a second segment, the first segment connected to the base member and having a cut-out portion defining a first hinge allowing the first segment to pivot about the base member, the first segment having a first projection configured to be positioned proximate the membrane when the base member is mounted on the container, the first segment having a first position wherein the first projection is configured to be spaced from the outer wall, the second segment connected to the first segment at a first interface area, the first interface area having a cut-out portion defining a second hinge allowing the second segment to pivot about the first segment, the second segment having a first depending rib;
a second extending member projecting from the base member, the second extending member positioned on the container generally in opposed relation to the first extending member, the second extending member having a first segment and a second segment, the first segment connected to the base member and having a cut-out portion defining a third hinge allowing the first segment of the second extending member about the base member, the first segment of the second extending member having a second projection configured to be positioned proximate the membrane when the base member is mounted on the container, the first segment of the second extending member having a first position wherein the second projection is configured to be spaced from the outer wall, the second segment of the second extending member connected to the first segment of the second extending member at a second interface area, the second interface area having a cut-out portion defining a fourth hinge allowing the second segment of the second extending member to pivot about the first segment of the second extending member, the second segment of the second extending member having a second depending rib; and,
a porous member positioned in the opening defined by the second chamber,
wherein in response to a user deflecting the first segment of the first extending member and the first segment of the second extending member towards one another about the respective first hinge and second hinge to respective deflected positions wherein the first projection if configured to deflect the outer wall proximate the membrane and wherein the second projection is configured to deflect the outer wall proximate the membrane wherein the weld seam is configured to fracture creating an opening through the membrane configured to allow the flowable material to pass from the first chamber, past the membrane, and into the second chamber, wherein the flowable material is configured to contact the porous member and be dispensed from the porous member, wherein in response to a user deflecting the second segment of the first extending member and the second segment of the second extending member about the respective third and fourth hinges to respective deflected positions, the first depending rib and the second depending rib are configured to deflect the outer wall proximate the first chamber to force further flowable material from the first chamber and into the second chamber to be dispensed from the porous member.

15. A dispenser actuator assembly for actuating a dispenser for dispensing a flowable material, the dispenser in the form of a plastic ampoule assembly having a container having an outer wall and membrane collectively defining a first chamber containing the flowable material, the membrane having a thickness and a weld seam, the weld seam having a thickness less than the thickness of the membrane, the dispenser actuator assembly comprising:
a base member having an opening configured to mount on the container; and
a fracturing mechanism operably connected to the container, the fracturing mechanism having an extending member projecting from the base member, the extending member having a projection configured to be positioned proximate the membrane, wherein in response to deflection of the extending member, the projection if configured to deflect the outer wall proximate the membrane wherein the weld seam is configured to fracture creating an opening through the membrane and configured to allow the flowable material to pass therethrough and from the dispenser.

16. The dispenser actuator assembly of claim 15 wherein the projection has a first end connected to the extending member and a second end connected to the base member.

17. The dispenser actuator assembly of claim 15 wherein the projection depends from an underside of the extending member.

18. The dispenser actuator assembly of claim 15 wherein the extending member covers the projection.

19. The dispenser actuator assembly of claim 15 wherein the projection has a length that is configured to extend beyond the membrane.

20. The dispenser actuator assembly of claim 15 wherein the projection depends from an underside of the extending member, the projection having a distal end, wherein when the base member is configured to be connected to the container, no space is present between the distal end of the projection and the outer wall of the container.

21. The dispenser actuator assembly of claim 15 wherein the extending member has a contoured surface.

22. The dispenser actuator assembly of claim 15 wherein the extending member has a concave outer surface.

23. The dispenser actuator assembly of claim 15 wherein the extending member is dimensioned to receive a thumb pad of a user.

24. The dispenser actuator assembly of claim 15 wherein the dispenser defines a longitudinal axis, the extending member has a first segment and a second segment connected to the first segment, the first segment extending from the outer wall, the second segment extending from the first segment along an axis configured to be generally parallel to the longitudinal axis.

25. The dispenser actuator assembly of claim 15 wherein the fracturing mechanism comprises a first fracturing mechanism and a second fracturing mechanism, the first fracturing mechanism and the second fracturing mechanism positioned on the base member in opposed relation.

26. A dispenser actuator assembly for actuating a dispenser for dispensing a flowable material, the dispenser in the form of a plastic ampoule assembly having a container having an outer wall and membrane collectively defining a first chamber configured to contain the flowable material, the membrane having a thickness and a weld seam, the weld seam having a thickness less than the thickness of the membrane, the container defining a longitudinal axis, the dispenser actuator assembly comprising:
   a base member having an opening configured to mount on the container; and
   a fracturing mechanism operably connected to the base member, the fracturing mechanism having a first extending member and a second extending member, the first extending member and the second extending member positioned on the base member in spaced relation, wherein the first extending member and the second extending member are configured to extend above the longitudinal axis, wherein in response to deflection of the extending members towards one another, the outer wall is configured to be deflected proximate the membrane wherein the weld seam is configured to be fractured creating an opening through the membrane configured to allow the flowable material to pass therethrough and from the dispenser.

27. The dispenser actuator assembly of claim 26 wherein the base member comprises a collar configured to be positioned on the outer wall of the container.

28. The dispenser actuator assembly of claim 27 wherein the outer wall of the container is cylindrical and has a cylindrical contour, wherein the collar is configured to be connected to the container along the cylindrical contour of the outer wall.

29. The dispenser actuator assembly of claim 27 wherein the collar has a passageway between the first extending member and the second extending member, the passageway in communication with the opening.

30. The dispenser actuator assembly of claim 27 wherein the extending members extend from the collar.

31. The dispenser actuator assembly of claim 27 wherein the collar has a length configured to extend beyond the membrane when the base member is configured to be mounted on the container.

32. The dispenser actuator assembly of claim 26 wherein the first extending member has a first segment and a second segment connected to the first segment of the first extending member, the first segment extending from the base member, the second segment extending from the first segment in a direction configured to be along an axis generally parallel to the longitudinal axis.

33. The dispenser actuator assembly of claim 26 wherein the first extending member and the second extending member are configured to be positioned on the container in a radially spaced relation and at locations above the longitudinal axis of the container.

34. A dispenser and actuator assembly comprising:
   a dispenser comprising a container having an outer wall and membrane collectively defining a first chamber configured to contain the flowable material, the membrane having a thickness and a weld seam, the weld seam having a thickness less than the thickness of the membrane, the container defining a longitudinal axis; and
   an actuator assembly having a base member slidably mounted on the container; and a fracturing mechanism operably connected to the base member, the fracturing mechanism comprising a first extending member and a second extending member, the first extending member and the second extending member positioned on the base member in spaced relation, wherein in response to deflection of the extending members towards one another, the outer wall deflects proximate the membrane wherein the weld seam fractures creating an opening through the membrane configured to allow the flowable material to pass therethrough and from the dispenser, wherein a plane is defined through the longitudinal axis wherein the first extending member and the second extending member are remote from the plane.

* * * * *